United States Patent [19]

Magda et al.

[11] Patent Number: 5,607,924
[45] Date of Patent: Mar. 4, 1997

[54] DNA PHOTOCLEAVAGE USING TEXAPHYRINS

[75] Inventors: Darren Magda, Cupertino, Calif.; Jonathan L. Sessler, Austin, Tex.; Brent L. Iverson, Austin, Tex.; Petra I. Sansom, Austin, Tex.; Meredith Wright, San Jose, Calif.

[73] Assignees: Pharmacyclics, Inc., Sunnyvale, Calif.; Board of Trustees, Univ. of TX Sys., Austin, Tex.

[21] Appl. No.: 469,177

[22] Filed: Jun. 6, 1995

Related U.S. Application Data

[63] Continuation-in-part of Ser. No. 310,501, Sep. 21, 1994, which is a continuation-in-part of Ser. No. 112,872, Aug. 25, 1993, Pat. No. 5,451,576, PCT/US94/06284, Jun. 9, 1994, which is a division of Ser. No. 822,964, Jan. 21, 1992, Pat. No. 5,242,429, which is a continuation-in-part of Ser. No. 227,370, Apr. 14, 1994, which is a continuation-in-part of Ser. No. 75,123, Jun. 9, 1993, abandoned, which is a continuation-in-part of Ser. No. 822,964, Jan. 21, 1992.

[51] Int. Cl.$^6$ .................. A61K 31/40; A61K 31/555
[52] U.S. Cl. .................. 514/44; 514/185; 514/410; 424/9.6; 424/9.61; 435/6; 436/98
[58] Field of Search .................. 514/44, 185, 410; 424/9.6, 9.61; 435/6; 436/98

[56] References Cited

U.S. PATENT DOCUMENTS

| | | | |
|---|---|---|---|
| 4,318,825 | 3/1982 | Frame | 252/428 |
| 4,647,447 | 3/1987 | Gries et al. | 524/9 |
| 4,835,263 | 5/1989 | Nguyen et al. | 536/27 |
| 4,878,891 | 11/1989 | Judy et al. | 604/5 |
| 4,880,008 | 11/1989 | Lauffer | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,141,911 | 8/1992 | Meunier et al. | 502/159 |
| 5,162,509 | 11/1992 | Sessler et al. | 534/15 |
| 5,242,797 | 9/1993 | Hirschfeld | 435/7 |
| 5,252,720 | 10/1993 | Sessler et al. | 534/11 |
| 5,256,399 | 10/1993 | Sessler et al. | 424/9 |
| 5,272,056 | 12/1993 | Burrows et al. | 435/6 |
| 5,272,142 | 12/1993 | Sessler et al. | 514/185 |
| 5,292,414 | 3/1994 | Sessler et al. | 204/157.5 |
| 5,302,714 | 4/1994 | Sessler et al. | 540/472 |
| 5,369,101 | 11/1994 | Sessler et al. | 534/13 |
| 5,371,199 | 12/1994 | Therien et al. | 534/11 |
| 5,432,171 | 7/1995 | Sessler et al. | 514/185 |
| 5,439,570 | 8/1995 | Sessler et al. | 254/157.17 |
| 5,451,576 | 9/1995 | Sessler et al. | 514/185 |
| 5,457,183 | 10/1995 | Sessler et al. | 534/11 |

FOREIGN PATENT DOCUMENTS

| | | |
|---|---|---|
| 0111418 | 6/1984 | European Pat. Off. |
| 0196515 | 10/1986 | European Pat. Off. |
| 0214908 | 3/1987 | European Pat. Off. |
| 0233701A2 | 8/1987 | European Pat. Off. |
| 2697254 | 4/1994 | France |
| WO90/02747 | 3/1990 | WIPO |
| 90/01208 | 8/1990 | WIPO |
| WO90/10633 | 9/1990 | WIPO |
| 91/19730 | 12/1991 | WIPO |
| 92/01781 | 2/1992 | WIPO |
| WO93/14093 | 7/1993 | WIPO |
| WO94/09003 | 4/1994 | WIPO |
| WO94/29316 | 12/1994 | WIPO |
| WO95/21845 | 8/1995 | WIPO |

OTHER PUBLICATIONS

Casas et al., "Preparation of Hybrid DNA Cleaver–Oligonucleotide Molecules Based on a Metallotris(methylpyridiniumyl)porphyrin Motif," *Bioconjugate Chem.*, 4:366–371 (1993).

Abid et al., "Lanthanide Complexes of Some Macrocyclic Schiff Bases Derived from Pyridine–2,6–dicarboxaldehyde and α, ω–Primary Diamines", *Inorg. Chim. Acta.* 95:119–125, 1984.

Acholla et al., "Binucleating Tetrapyrrole Macrocycles", *J. Am. Chem. Soc.*, 107:6902–6908, 1985.

Acholla et al., "A Binucleating Accordian Tetrapyrrole Macrocycle", *Tetrahedron Lett.*, 25:3269–3270, 1984.

Ansell, "X–Ray Crystal Structure of the Pentagonal Bipyramidal Nickel (11) Complex [Ni$^{11}$(L) (H$_2$O)$_2$](BF$_4$)$_2$ and the Selective Stabilisation of the Nickel (1) Oxidation State by a Quinquedentate Macrocyclic Ligand", *J. Chem. Soc., Chem. Commun.* pp. 546–547, 1982.

Bauer et al., "Sapphyrins: Novel Aromatic Pentapyrrolic Macrocycles", *J. Am. Chem. Soc.*, 105:6429–6436, 1983.

Broadhurst et al., "Preparation of Some Sulphur–containing Polypyrrolic Macrocycles. Sulphur Extrusion from a meso–Thiaphlorin", *J. Chem. Soc., Chem. Commun.* pp. 807–809, 1970.

Broadhurst et al., "18–and 22–π–Electron Macrocycles Containing Furan, Pyrrole, and Thiophen Rings", *J. Chem. Soc., Chem. Commun.* pp. 1480–1482, 1969.

Broadhurst et al., "New Macrocyclic Aromatic Systems Related to Porphins", *J. Chem. Soc., Chem. Commun.* pp. 23–24, 1969.

Broadhurst et al., "The Synthesis of 22 π–Electron Macrocycles. Sapphyrins and Related Compounds", *J. Chem. Soc. Perkin Trans.*, 1:2111–2116, 1972.

Cuellar et al., "Synthesis and Characterizatioin of Metallo and Metal–Free Octaalkylphthalocyanines and Uranyl Decaalkysuperphthalocyanines", *Inorg. Chem.*, 20:3766–3770, 1981.

(List continued on next page.)

Primary Examiner—Richard L. Raymond
Attorney, Agent, or Firm—Jacqueline S. Larson

[57] ABSTRACT

Methods of cleavage of a polymer of deoxyribonucleic acid using photosensitive texaphyrins are disclosed. A preferred method of use is the site-specific cleavage of a polymer of deoxyribonucleic acid and a preferred texaphyrin is a derivatized texaphyrin having binding specificity, in particular, a texaphyrin covalently coupled to a site-directing molecule, preferably an oligonucleotide.

20 Claims, 4 Drawing Sheets

OTHER PUBLICATIONS

Day et al., "Large Metal Ion–Centered Template Reactions. A Uranyl Complex of Cyclopentakis (2–iminoisoindoline)", *J. Am. Soc.*, 97:4519–4527, 1975.

De Cola et al., "Hexaaza Macrocyclic Complexes of the Lanthanides", *Inorg. Chem.*, 25:1729–1732, 1986.

Dougherty, "Photosensitizers: Therapy and Detection of Malignant Tumors", *Photochem. Photobiol.*, 45:879–889, (1987).

Gosmann et al., "Synthesis of a Fourfold Enlarged Porphyrin with an Extremely Large, Diamagnetic Ring–Current Effect", *Angew, Chem., Int. Ed Engl.*, 25:1100–1101, (1986).

Gossauer, "Syntheses of Some Unusual Polypyrrole Macrocycles", *Bull. Soc. Chim. Belg.*, 92:793–795, (1983).

Knubel et al., "Biomimetic Synthesis of an Octavinylogous Porphyrin with an Aromatic [34] Annulene System", *Angew. Chem., Int. Ed. Engl.*, 27:1170–1172, 1988.

Lauffer, "Paramagnetic Metal Complexes as Water Proton Relaxation Agents for NMR Imaging: Theory and Design", *Chem. Rev.*, 87:901–927, 1987.

LeGoff et al., "Synthesis of a [1,5,1,5] Platyrin, a 26 $\pi$–Electron Tetrapyrrolic annulene", *J. Org. Chem.*, 52:710–711, 1987.

Marks et al., "Large Metal Ion–Centered Template Reactions. Chemical and Spectral Studies of the Superphthalocyanine Dioxocyclopentakis (1–iminoisoindolinato) uranium (VI) and Its Derivatives", *J. Am. Chem. Soc.*, 100:1695–1705, 1978.

Rexhausen et al., "The Synthesis of a New 22 $\pi$–Electron Macrocycle: Pentaphyrin", *J. Chem. Soc., Chem. Commun.*, p. 275, 1983.

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate Porphyrin–Like Ligands", *Comm. Ing. Chem.*, 7:333–350, 1988.

Sessler et al., "An Expanded Porphyrin: The Synthesis and Structure of a New Aromatic Pentadentate Ligand", *J. Am. Chem. Soc.*, 110:5586–5588, 1988.

Tweedle et al., "Principles of Contrast–Enhanced MRI, in Magnetic Resonance Imaging," 2nd ed. Partain, et al, Eds., W. B. Saunders: Philadelphia, vol. I (1988) 793–809.

Vogel et al., "Porphycene –a Novel Porphin Isomer", *Angew. Chem., Int. Ed. Engl.*, 25:257–259, 1986.

Vogel et al., "2, 7, 12, 17–Tetrapropylporphycene –Counterpart of Octaethylporphyrin in the Porphycene Series", *Angew. Chem., Int. Ed. Engl.*, 26:928–931, 1987.

Sessler et al., "A Water–Stable Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadmium Expanded Porphyrin: Solution and X–ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. Soc., Chem. Commun.*, 314–316, 1989. Submitted as A32 in 1449 for UTSB:458.

Sessler et al., "Expanded Porphyrins: The synthesis and Metal Binding Properties of Novel Tripyrrane–Containing Macrocycles", *J. Coord. Chem.*, 18:99–104, 1988.

Sessler et al., "The Synthesis and Structure of a Novel 22 $\pi$–Electron Aromatic Pentadentate Macrocyclic Ligand: An Expanded Porphyrin", Toronto ACS Meeting, Jun. 1988. USA.

Sessler et al., "A Water–Stable Gadolinium (III) Complex Derived from a New Pentadentate", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived (Texaphyrin–type) Macrocycles: Potential Photosensitizers Which Absorb in the Far–red Spectral Region", *SPIE, Optical Methods for Tumor Treatment and Early Diagnosis: Mechanism and Technique*, 1426:318–329, 1991.

Sessler et al., "'Texaphyrin': A Novel 22 $\pi$–Electron Aromatic Pentadentate Macrocyclic Ligand", *ACS meeting*, Los Angeles, Sep. 1988.

Sessler and Burrell, "Expanded Porphyrins," *Topics in Current Chemistry*, 161:180–273, 1991.

Sessler et al., "Synthesis and Structural Characterization of Lanthanide (III) Texaphyrins," *Inorganic Chemistry*, 32(14):3175–3187, 1993.

"2–Äthylamino–2–methyl–propanol–(1)", *Beilstein's Handbuch*, 4:785, 1950.

"Tentative Rules for Carbohydrate Nomenclature Part 1 (1969)," *Handbook of Biochemistry and Molecular Biology*, 3rd ed., Fasman, Ed., CRC Press, Cleveland, Ohio, pp. 100–102.

Sessler et al., "Preparation of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Washington, DC.

Sessler et al., "Synthesis and Applications of Schiff–Base Derived Expanded Porphyrins," *Abstracts of Papers*, Part 1, 204th ACS Nathional Meeting, Aug. 23–28, 1992, Washington, DC.

Sessler, Jonathan L., "Texas–Sized Molecule," *Discovery*, 13(1):44–49,1993.

Sessler et al., "Photodynamic Inactivation of Enveloped Viruses Using Sapphyrin, $\alpha 22$ $\pi$–Electron Expanded Porphyrin: Possible Approaches to Prophylactic Blood Purification Protocols", *SPIE Photodynamic Therapy: Mechanisms II*. 1203:233–245, 1990.

Maiya et al., "Ground–and Excited–State Spectral and Redox Properties of Cadmium(II) Texaphyrin," *Journal of Physical Chemistry*, 93(24):8111–8115, 1989.

Sessler et al., "Texaphyrins: Synthesis and Applications," *Accounts of Chemical Research*, 27(2):43–50, 1994.

Leff, "Texas 'Son–of–Porphyrin' Molecule Lassos Europium to Kill Drug Resistance Gene," *BioWorld Today*, 5(156):1, 1994.

Young et al., "Preclinical Evaluation of Gadolinium (III) Texaphyrin Complex. A New Paramagnetic Contrast Agent for Magnetic Resonance Imaging," *Investigative Radiology*, 29(3):330–338, 1994.

Dietrich et al., "Proton Coupled Membrane Transport of Anions Mediated by Cryptate Carriers," *J. Chem. Soc. Chem. Comm.*, 1988, 11:691–692.

Dixon et al., "Molecular Recognition: Bis–Acylguanidiniums Provide a Simple Family of Receptors for Phosphodiesters," *J. Am. Chem. Soc.*, 1992, 114:365–366.

Furuta et al., "Enhanced Transport of Nucleosides and Nucleoside Analogues with Complementary Base–Pairing Agents," *Journal of the American Chemical Society*, 1991, 113:4706–4707.

Galán et al., "A Synthetic Receptor for Dinucleotides," *J. Am. Chem. Soc.*, 1991, 113:9424–9425.

Galán et al., "Selective Complexation of Adenosine Monophosphate Nucleotides By Rigid Bicyclic Guanidinium Abiotic Receptors," *Tetrahedron Letters*, 32(15):1827–1830, 1991.

Hisatome et al., "Porphyrins Coupled with Nucleoside Bases. Synthesis and Characterization of Adenine–and Thymine–Porphyrin Derivatives," *Chemistry Letters*, 1990, 2251–2254.

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J. Am. Chem. Soc.*, 1990, 112:3896–3904.

Hosseini et al., "Multiple Molecular Recognition and Catalysis. Nucleotide Binding and ATP Hydrolysis by a Receptor Molecule Bearing an Anion Binding Site, an Intercalator Group, and a Catalytic Site," *J. Chem. Soc. Chem. Comm.*, 1988, 9:596–598.

Kimura et al., "A Study of New Bis(macrocyclic polyamine) Ligands as Inorganic and Organic Anion Receptors," *J. Org. Chem.*, 1990, 55(1):46–48.

Kimura, "Macrocyclic Polyamines as Biological Cation and Anion Complexones—An Application to Calculi Dissolution," 113–141, Topics in Current Chremistry (1985).

Li and Diederich, "Carriers for Liquid Membrane Transport of Nucleotide 5'-Triphosphates," *J. Org. Chem.*, 1992, 47:3449–3454.

Marks and Stojakowvic, "Large Metal Ion–Centered Template Reactions. Chemical and Spectral Studies of the Superphthalocyanine Dioxocyclopentakis (1–iminoisoindolinato)uranium(VI) and Its Derivatives," *J. Am. Chem. Soc.*, 1978, 1695–1705.

Schmidtchen, "A Non–Macrocyclic Host for Binding Organic Phosphates in Protic Solvents," *Tetrahedron Letters*, 1989, 30(34):4493–4496.

Seel and Vogtle, "Molecular Recognition and Transport of Nucleobases—Superiority of macrobicyclid Host Molecules," *Angew, Chem. Int. Ed. Engl.*, 1991, 30(4):442–444.

Sessler et al., "Anion Binding: A New Direction In Porphyrin–Related Research," *Pure & Applied Chem.*, 65(3):393–398, 1993.

Sessler et al., "Cytosine Amine Derivatives," *J. Org. Chem.*, 1992, 47:826–834.

Aoyama et al., "Multi–Point Interaction of Phosphates with Protonated Pyridylporphyrin. Discrimination of Monoalkyl and Dialkyl Phosphates," *Chemistry Letters*, 1241–1244 (1991).

Claude et al., "Binding of Nucleosides, Nucleotides and Anionic Planar Substrates by Bis–Intercaland Receptor Molecules," *J. Chem. Soc. Chem. Commun.*, 1991, 17:1182–1185.

Cramer et al., "Synthesis and Structure of the Chloride and Nitrate Inclusion Complexes of [16–Pyrimidinium crown–4]," *J. Am. Chem. Soc.*, 1991, 113:7033–7034.

Tabushi et al., "Lipophilic Diammonium Cation Having a Rigid Structure Complementary to Pyrophosphate Dianions of Nucleotides. Selective Extraction and Transport of Nucleotides," *J. Am. Chem. Soc.*, 1981, 103:6152–6157.

Tohda et al., "Liquid Membrane Electrode for Guanosine Nucleotides Using a Cytosine–Pendant Triamine Host as the Sensory Element," *Analytical Chemistry*, 1992, 64(8):960–964.

Nam–Chiang Wang et al., "Pyrrole chemistry. XVII. Alkylation of the pyrrolyl ambident anion," *Can. J. Chem.*, 55:4112–4116,1977.

T. D. Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler et al., "Gadolinium (III) Texaphyrin: A Novel MRI Contrast Agent," *Journal of the American Chemical Society*, 115(22):10, 368–10,369, 1993.

Iverson et al., "Interactions Between Expanded Porphyrins and Nucleic Acids," *Pure Applied Chemistry*, 66(4):845–850, 1994.

Matthews et al., "Inactivation of Viruses with Photoactive Compounds," *Blood Cells*, 18(1):75–89, 1992.

Ehrenberg et al., "Spectroscopy, Photokinetics and Cellular Effect of Far–Red and Near Infrared Absorbing Photosensitizers," *Proc. SPIE–Int. Soc. Opt. Eng 1992, 1645 (Proc. Opt. Methods Tumor Treat. Dect.: Mech. Tech. Photodyn. Ther.*, 259–263, 1992.

Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Koenig et al., "PDT of Tumor–Bearing Mice Using Liposome Delivered Texaphyrins," International Conference, Milan, Italy, Biosis citation only, Jun. 24–27, 1992.

Goodchild, John, "Conjugates of Oligonucleotides and Modified Oligonucleotides: A Review of Their Synthesis and Properties," *Bioconjugate Chemistry*, 1(3):165–187, 1990.

Kobayashi et al., "Uptake of Chlorophyll–Derivatives by Cellular Nuclei and Mitochondria," *Photomed. Photobiol.*, 15:75–84, 1993.

Brown and Truscott, "New Light on Cancer Therapy," *Chemistry in Britain*, 955–958, 1993.

Lin et al., "Use of EDTA Derivatization to Characterize Interactions between Oligodeoxyribonucleoside Methylphosphonates and Nucleic Acids," *Biochemistry*, 28:1054–1061, 1989.

Strobel and Dervan, "Cooperative Site Specific Binding of Oligonucleotides to Duplex DNA," *Journal of the American Chemical Society*, 111(18):7286–7287, 1989.

Dreyer and Dervan, "Sequence–specific Cleavage of Single–Stranded DNA: Oligodeoxynucleotide–EDTA.Fe(II)," *Proc. Natl. Acad. Sci. USA*, 82:968–972, 1985.

Doan et al., "Sequence–targeted Chemical Modifications of Nucleic Acids by Complementary Oligonucleotides Covalently Linked to Porphyrins," *Nucleic Acids Research*, 15(21):8643–8659, 1987.

Doan et al., "Targeted Cleavage of Polynucleotides by Complementary Oligonucleotides Covalently Linked to Iron–Prophyrins," *Biochemistry*, 26:6736–6739, 1986.

Dervan, Peter B., "Design of Sequence–Specific DNA–Binding Molecules," *Science*, 232:464–471, 1986.

Groves and Farrell, "DNA Cleavage by a Metal Chelating Tricationic Porphyrin," *J. Am. Chem. Soc.*, 111:4998–5000, 1989.

Fiel, Robert J., "Porphyrin–Nucleic Acid Interactions: A Review," *Journal of Biomolecular Structure & Dynamics*, 6(6):1259–1275, 1989.

Vlassov et al., "Photoactivatable Porphyrin Oligonucleotide Derivatives for Sequence Specific Chemical Modification and Cleavage of DNA," *Nucleosides & Nucleotides*, 10(1–3):641–643, 1991.

Zuk et al., "Pharmacokinetic and Tissue Distribution Studies of the Photosensitizer bis(Di–Isobutyl Octadecysiloxy)Silicon 2,3–Naphthalocyanine (isoBosinc) in Normal and Tumor–Bearing Rats," *Photochemistry and Photobiology*, 59(1):66–72, 1994.

Lee et al., "Interaction of Psoralen–Derivatized Oligodeoxyribonucleoside Methylphosphonates with Single–Stranded DNA," *Biochemistry*, 27:3197–3203, 1988.

Bhan and Miller, "Photo–Cross Linking of Psoralen–Derivatized Oligonucleoside Methylphosphonates to Single–Stranded DNA," *Bioconjugate Chem.*, 1:82–88, 1990.

Boutorine et al., "Fullerene–Oligonucleotide Conjugates: Photo–Induced Sequence Specific DNA Cleavage", *Agnew. Chem. Int. Ed. Engl.*, 33(23/24):2462–2465, 1994.

Dolphin et al., "Porphocyanine: An Expanded Tetrapyrrolic Macrocycle," *J. Am. Chem. Soc.*, 115:9301–9302, 1993.

Ehrenberg et al., "The Binding and Photosensitization Effects of Tetrabenzoporphyrins and Texaphyrin in Bacterial Cells," *Lasers in Medical Science*, 8:197–203, 1993.

Le Doan et al., "Sequence–Targeted Photochemical Modifications of Nucleic Acids by Complementary Oligonucleotides Covalently Linked to Porphyrins," *Bioconjugate Chem.*, 1:108–113, 1990.

Le Doan et al., "Sequence–Specific Recognition, Photocrosslinking and Cleavage of the DNA Double Helix by an Oligo–[α]–Thymidylate Covalently Attached to an Azidoproflavine," *Nucleic Acids Res.*, 15:7749–7760, 1987.

Levina et al., "Photomodification of RNA and DNA Fragments by Oligonucleotide Reagents Bearing Arylazide Groups," *Biochimie*, 75:25–27, 1993.

Mastruzzo et al., "Targeted Photochemical Modification of HIV–Derived Oligoribonucleotides by Antisense Oligodeoxynucleotides Linked to Porphyrins," *Photochem. Photobiol.*, 60(4):316–322, 1994.

Fedorova et al., "Palladium(II)–Coproporphyrin I as a Photoactivable Group in Sequence–Specific Mofidification of Nucleic Acids by Oligonucleotide Derivatives," *FEBS Lett.*, 259(2):335–337, 1990.

Morgan and Skalkos, "Second Generation Sensitizers: Where are We and Where Should We Be Going?" *Proc. SPIE Int. Soc. Opt. Eng. Ser.*, 6:87–106, 1990.

Perrouault et al., "Sequence–Specific Artificial Photo–Induced Endonucleases Based on Triple Helix–Forming Oligonucleotides," *Nature*, 344:358–360, 1990.

Pieles and Englisch, "Psoralen Covalently Linked to Oligodeoxyribonucleotides: Synthesis, Sequence Specific Recognition of DNA and Photo–Cross–Linking to Pyrimidine Residues of DNA," *Nucleic Acids Res.*, 17(1):285–299, 1989.

Praseuth et al., "Sequence–Targeted Photosensitized Reactions in Nucleic Acids by Oligo–α–Deoxynucleotides and Oligo–β–Deoxynucleotides Covalently Linked to Proflavin," *Biochemistry*, 27:3031–3038, 1988.

Praseuth et al., "Sequence–Specific Binding and Photocrosslinking of α and β Oligodeoxynucleotides to the Major Groove of DNA via Triple–Helix Formation," *Proc. Natl. Acad. Sci. USA*, 85:1349–1353, 1988.

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Natl. Acad. Sci. USA*, 88:5602–5606, 1991.

Teare and Wollenzien, "Specificity of Site Directed Psoralen Addition to RNA," *Nucleic Acids Res.*, 17(9):3359–3372, 1989.

Vogel et al., "New Porphycene Ligands: Octaethyl–and Etioporphycene (OEPc and EtioPc)–Tetra–and Pentacoordinated Zinc Complexes of OEPc," *Angew. Chem. Int. Ed. Engl.*, 32(11):1600–1604, 1993.

Wessel et al., "Porphyrins with Aromatic 26π–Electron Systems," *Agnew. Chem. Int. Ed. Eng.*, 32(8):1148–1151, 1993.

Agrawal et al., "Cellular Uptake and Anti–HIV Activity of Oligonucleotides and Their analogs," *Gene Regulation: Biology of Antisense RNA and DNA*, 273–283, 1992.

Agrawal and Tang, "Efficient Synthesis of Oligoribonucleotide and Its Phosphorothioate Analogue Using H–Phosphonate Approach," *Tetrahedron Letters*, 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Basile et al., "Metal–Activated Hydrolytic Cleavage of DNA," *J. Am. Chem. Soc.*, 109:7550–7551, 1987.

Bradley et al., "Antisense Therapeutics," *Gene Regulation: Biology of Antisense RNA and DNA*, 285–293, 1992.

Breslow et al., "Effects of Metal Ions, Including $Mg^{2+}$ and Lanthanides, on the Cleavage of Ribonucleotides and RNA Model Compounds," *Proc. Natl. Acad. Sci. USA*, 88:4080–4083, 1991.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13):4951–4958, 1992.

Chin and Banaszczyk, "Rate–Determining Complexatioin in Catalytic Hydrolysis of Unactivated Esters in Neutral Water," *J. Am. Chem. Soc.*, 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.*, 111:4103–4105, 1989.

Chin et al., "Co(III) Complex Promoted hydrolysis of Phosphate Diesters: Comparison in Reactivity of Rigid cis–Diaquotetraazacobalt(III) Complexes," *J. Am. Chem. Soc.*, 111:186–190, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," *Tetrahedron Letters*, 31(38):5413–5416, 1990.

Cohen, Jack S., "Chemically Modified Oligodeoxynucleotide Analogs as Regulators of Viral and Cellular Gene Expression" *Gene Regulation: Biology of Antisense RNA and DNA*, 247–259, 1992.

Furuta et al., "Phosphate Anion Binding: Enhanced Transport of Nucleotide Monophosphates Using a Sapphyrin Carrier," *J. Am. Chem. Soc.*, 113:6677–6678, 1991.

Hanvey et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am. Chem. Soc.*, 111:2521–2527, 1989.

Kim and Chin, "Dimethyl Phosphate Hydrolysis at Neutral pH," *J. Am. Chem.Soc.*, 114:9792–9795, 1992.

Komiyama et al., "Unprecedentedly Fast Hydrolysis of the RNA Dinucleoside Monophosphates ApA and UpU by Rare Earth Metal Ions," *J. Chem. Soc. Chem. Commun.*, 640–641, 1992.

Menger et al., "Phosphate Ester Hydrolysis Catalyzed by Metallomicelles," *J. Am. Chem. Soc.*, 109:2800–2803, 1987.

Modak et al., "Toward Chemical Ribonucleases. 2. Synthesis and Characterization of Nucleoside–Bipyridine Conjugates. Hydrolytic Cleavage of RNA by Their Copper(II) Complexes," *J. Am. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications," *J. Am. Chem. Soc.*, 114:1903–1905, 1992.

Ranganathan et al., "Design of a Chemical Nuclease Model with (Lys)$_2$Cu as the Core Motif," *Journal of the Chemical Society*, 4:337–339, 1993.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remarkably Fast Hydrolysis of 3',5'–Cyclic Adenosine Monophosphate by Cerium(III) Hydroxide Cluster," *J. Chem. Soc. Chem. Comm.*, 2 pages, 1992.

To and Neiman, "The Potential For Effective Antisense Inhibition of Retroviral Replication Medicated by Retrovial Vectors," *Gene Regulation: Biology of Antisense RNA and DNA*, 261–271, 1992.

Shelton and Morrow, "Catalytic Transesterification and Hydrolysis of RNA by Zinc(II) Complexes," *Inorg. Chem.*, 30:4295–4299, 1991.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Kolasa et al., "Trivalent Lanthanide Ions Do Not Cleave RNA in DNA–RNA Hybrids", *Inorg. Chem.*, 32:3983–3984, 1993.

Schneider et al., "Catalysis of the Hydrolysis of Phosphoric Acid Diesters by Lanthanide Ions and the Influence of Ligands," *Angew. Chem. Int. Ed. Engl.*, 32(12):1716–1719, 1993.

Hayashi et al., "Site–Selective Hydrolysis of tRNA by Lanthanide Metal Complexes," *Inorg. Chem.*, 32:5899–5900, 1993.

Magda et al., "Sequence–Specific Photocleavage of DNA by an Expanded Porphyrin with Irradiation Above 700 nm," *J. Am. Chem. Soc.*, 117:3629–3630, 1995.

Sessler et al., "Expanded Porphyrins. Receptors for Cationic, Anionic, and Neutral Substrates, in Transition Metals in Supramolecular Chemistry" L. Fabbrizzi and A. Poggi, Editors, NATO ASI Series, Kluwer, Amsterdam, pp. 391–408, 1994.

DNA PHOTOCLEAVAGE USING TEXAPHYRINS

Research leading to the present invention was supported in part by the National Science Foundation (CHE 9122161) and the National Institutes of Health (AI 33577 and AI 28845). The U.S. government therefore has certain rights in the invention.

This application is a continuation-in-part application of U.S. Ser. No. 08/310,501, filed Sep. 21, 1994, which is a continuation-in-part application of U.S. Ser. No. 08/112,872 filed Aug. 25, 1993, now U.S. Pat. No. 5,451,576 and of International application No. PCT/US94/06284 designating the United States and filed Jun. 9, 1994. U.S. Ser. No. 08/112,872 is a divisional application of U.S. Ser. No. 07/822,964 filed Jan. 21, 1992, now U.S. Pat. No. 5,252,720. PCT/US94/06284 is a continuation-in-part application of U.S. Ser. No. 08/227,370 filed Apr. 14, 1994, which is a continuation-in-part application of U.S. Ser. No. 08/075,123 filed Jun. 9, 1993, now abandoned, which is a continuation-in-part of U.S. Ser. No. 07/822,964 filed Jan. 21, 1992, now U.S. Pat. 5,252,720. All of the above-named patents are incorporated by reference herein.

FIELD OF THE INVENTION

The present invention relates to catalysts for the cleavage of DNA; in particular, photo-induced cleavage of DNA, especially site-specific cleavage in a biological system.

BACKGROUND OF THE INVENTION

Photodynamic therapy (PDT) is a treatment technique that uses a photosensitizing dye which localizes at, or near, the treatment site, and when irradiated in the presence of oxygen serves to produce cytotoxic materials, such as singlet oxygen ($O_2(^1\Delta_g)$), from benign precursors (e.g. $O_2(^3\Sigma_g^-)$). Other reactive species such as superoxide, hydroperoxyl, or hydroxyl radicals may be involved. At the doses used, neither the light nor the drug has any independent biological effect. In PDT, the photosensitizer acts in a 'catalytic' way, since its function is not to react directly with the cellular targets, but to absorb light energy and to transfer it to molecular oxygen, regenerating ground state photosensitizer.

The effectiveness of PDT is due to three additional factors: i) The photosensitive dyes used in PDT must have the ability to localize at the treatment site relative to surrounding tissue. ii) The high reactivity and short lifetime of activated oxygen means that it has a very short range and is unlikely to escape from the cell in which it is produced; cytotoxicity is therefore restricted to the precise region of tissue absorbing light, perhaps down to the cellular level. iii) Developments in lasers and fiber optics allow a beam of intense light to be delivered precisely to many parts of the body.

For reviews of photodynamic therapy, see U.S. Pat. No. 5,252,720 (incorporated by reference herein); Sindelar et al., (1991); Grossweiner, L. I., (1991); Henderson, B. W. and T. J. Dougherty, (1992); and Moan, J. and K. Berg, (1992). In recent years, considerable effort has been devoted to the synthesis and study of new photosensitizers (a review is found in Brown, S. B. and Truscott, T. G., 1993). The development of more effective photochemotherapeutic agents requires the synthesis of compounds which absorb in the spectral region where living tissues are relatively transparent (i.e., 700–1000 nm), have high triplet quantum yields, and are minimally toxic.

An effective photo-catalyst for PDT and DNA cleavage would have the following properties:
1. Easily available
2. Low intrinsic toxicity
3. Long wavelength absorption
4. Efficient photosensitizer for singlet oxygen production
5. Fair solubility in water
6. Selective uptake in lipophilic tissue such as atheroma or tumor tissue
7. Showing high affinity for enveloped viruses
8. Quick degradation and/or elimination after use
9. Chemically pure and stable
10. Easily subject to synthetic modification
11. Efficient at physiological temperature and pH
12. Specific for certain biological substrates
13. Easy administered to a biological system Photodynamic cleavage of DNA is known. For example, Praseuth et al., reported cleavage of plasmid DNA by synthetic water-soluble porphyrins with visible light in the presence of oxygen. Fiel, R. J. (1989) also reported the photosensitized strand cleavage and oxidative-reductive strand scission of DNA by iron porphyrins. In another example, Kobayashi et al. reported cleavage of plasmid DNA by sodium pheophorbide (a derivative of chlorophyll) with visible light in the presence of oxygen. Porphyrin-oligonucleotide derivatives were reportedly used to effect sequence specific modifications of DNA substrates followed by cleavage using hot piperidine (Vlassov et al., 1991; Le Doan et al., 1990). The absorption wavelengths for these porphyrin conjugates were below 700 nm, a range that does not penetrate tissue as effectively as longer wavelengths of light.

The use of ultraviolet light with the drug 8-methoxy-psoralen to treat psoriasis is well established. Lee et al. relates to the interaction of psoralen-derivatized oligodeoxyribonucleoside methylphosphonates with single-stranded DNA. Crosslinked photoadducts between pyrimidines and psoralen appear to form. This treatment may result in the development of cancerous cells. Furthermore, irradiation at the short wavelength of about 365 nm does not penetrate the body and is therefore only useful on the body surface. Psoralen-based treatments must allow the drug to leave the body before the patient is exposed to visible light or the reaction will continue on the skin surface.

Sequence-specific cleavage of DNA has also been reported for dark reactions using oligonucleotides derivatized with metal complexes. Some examples include oligonucleotide-EDTA-Fe complexes (Strobel, D. A. and P. B. Dervan, 1989; Lin, et al., 1989; Dreyer, G. B. and P. B. Dervan, 1985), oligonucleotide-tricationic porphyrins with metal binding appendages (Groves, J. T. and T. P. Farrell, 1989), oligonucleotide-phenanthroline-copper complexes (Chen, C. H. B. and D. S. Sigman, 1988), oligonucleotide-manganese-porphyrins (Meunier, B. et al., 1993), and iron-porphyrins linked to oligonucleotides (Le Doan et al., 1986, 1987).

All of the above examples of DNA cleavage have been directed to cleavage of single-stranded DNA. However, since cellular DNA is predominantly double-stranded, for practical use and effect in most instances it would be desirable to cleave double-stranded DNA. Oligonucleotide-derived therapeutics that target double-stranded DNA are referred to as anti-gene agents. Binding to double-stranded DNA is much less straight-forward than binding to RNA or single-stranded DNA (the antisense approach), since special Hoogsteen interactions must be used. Once bound, the anti-gene agent must be able to compete successfully with cellular factors in order to inhibit gene expression.

| LIST OF ABBREVIATIONS | |
|---|---|
| DCA | Dichloroacetic acid |
| DCC | Dicyclohexylcarbodiimide |
| DMAP | Dimethylaminopyridine |
| DMF | Dimethylformamide |
| DMT | Dimethoxytrityl protecting group |
| DMT-Cl | Dimethoxytrityl chloride |
| EDC | L-Ethyl-3-[3-(dimethylamino)propyl] carbodiimide |
| EDTA | Ethylenediamine tetraacetic acid |
| IPA | Isopropylalcohol |
| NHS | N-hydroxysuccinimide |
| NM | Nanometers |
| PTSA | p-Toluenesulfonic acid monohydrate |
| TEA | Triethylamine |
| TEAB | Triethylammonium bicarbonate |
| TFA | Trifluoroacetic acid |
| TsCl | Tosyl chloride |
| THF | Tetrahydrofuran |
| TXP(Tx) | Texaphyrin |

SUMMARY OF THE INVENTION

The present invention seeks to solve the problems found in the prior art by providing photosensitive texaphyrins and oligonucleotide conjugates thereof that provide biolocalization and/or are site-directing; have absorption in the physiologically important range of 700–900 nm; provide stable chelation for an otherwise toxic metallic cation; provide specificity for targeted sites in a therapeutic application; and are sufficiently nontoxic for in vivo use.

The present invention also involves the discovery that photosensitive texaphyrins catalyze the cleavage of a polymer of deoxyribonucleic acid. The DNA may be single-stranded or double-stranded. Cleavage is enhanced by the presence of oxygen, indicating that singlet oxygen or another oxygen by-product is the likely toxic agent. A photosensitive texaphyrin may be a diamagnetic metal texaphyrin complex or may be metal-free. Texaphyrins are unique molecules in that they chelate a metal in a very stable complex and, furthermore, allow for derivatization for various biological applications.

Thus, the present invention provides a method of light-induced cleavage of a polymer of deoxyribonucleic acid. The method comprises the steps of contacting the polymer with a photosensitive texaphyrin and exposing the photosensitive texaphyrin to light for a time sufficient to cleave the polymer. In a preferred embodiment, the exposing step is carried out in the presence of oxygen.

A texaphyrin as used herein is an aromatic pentadentate expanded porphyrin analog with appended functional groups. Such pendant groups may enhance solubility or biolocalization or may provide coupling sites for site-directing molecules such as oligonucleotides. The texaphyrin may be a metal complex of texaphyrin; preferred metals are diamagnetic metals.

The polymer may be a solution or a suspension of DNA or may be cellular DNA in vitro or in vivo. In the present light-dependent cleavage, the light may have a wavelength range of about 650–900 nm, preferably 700–800 nm, and most preferably 730–770 nm.

The cleavage of DNA described herein is a photolyric cleavage. It is believed that the cleavage is not hydrolyric where a water molecule is added across a bond to break the bond, nor is the cleavage believed to be solely oxidative where an oxidation reaction in the absence of light causes breakage of the bond.

It will be apparent to one of skill in the art in light of the present disclosure that the site-specific cleavage of DNA has important ramifications in a variety of applications. Potential particular applications for this process include antisense applications when the DNA is single-stranded; the specific cleavage and possible subsequent recombination of DNA; destruction of viral DNA; construction of probes for controlling gene expression at the cellular level and for diagnosis; and cleavage of DNA in footprinting analyses, DNA sequencing, chromosome analyses, gene isolation, recombinant DNA manipulations, mapping of large genomes and chromosomes, in chemotherapy, in site-directed mutagenesis, and the like.

Texaphyrins possess inherent biolocalization. Additionally, in one embodiment of the present invention, the texaphyrin metal complexes are further coupled to site-directing molecules to form conjugates for targeted in vivo delivery. "Specificity for targeted sites" means that upon contacting the texaphyrin-oligonucleotide conjugate with the targeted site, for example, under physiological conditions of ionic strength, temperature, pH and the like, specific binding will occur. The interaction may occur due to specific electrostatic, hydrophobic, entropic or other interaction of certain residues of the conjugate with specific residues of the target to form a stable complex under conditions effective to promote the interaction. In a preferred embodiment of the present invention, the interaction between a texaphyrin-oligonucleotide conjugate and the complementary deoxyribonucleic acid is an example of anti-gene technology and will allow cleavage of a polymer of DNA that is in the vicinity of the specific binding. The inherent biolocalization properties of texaphyrin further effect targeting of an anti-gene agent to certain biological regions, especially tumors and atheroma, for example.

This method of site-specific cleavage of DNA involves two sources of specificity. A complementary oligonucleotide is designed to base pair with the targeted substrate and the second source of specificity for in vitro or in vivo applications is the positioning of the laser light. Such positioning of laser light, either by manual or mechanical means, would be particularly advantageous when the oligonucleotide cleavage reaction in question is to be effected at a particular biological locus, such as, for instance, a deep-seated tumor site. Here, the fact that the texaphyrins absorb light at wavelengths where bodily tissues are relatively transparent (700–900 nm) is particularly advantageous. This procedure allows for the effective implementation of light-based oligonucleotide strategies at loci deep within the body with relatively little deleterious light-based photosensitization of other tissues where the texaphyrin conjugates are not localized.

The use of texaphyrin metal complexes to cleave DNA in vivo as a treatment procedure relies on the effective localization of the complex to the site of desired cleavage. A site of desired cleavage may be a position novel to undesired organisms in terms of health care. A site of desired cleavage may be a DNA encoding a product deleterious to the host or may be a normal DNA that is deleterious in some way. The binding of a conjugate to a DNA double helix will form a triple helix which has sufficient stability for effective cleavage to occur.

The texaphyrin-oligonucleotide conjugate would have immediate applications for anti-viral therapy as well as cancers (an oligonucleotide complementary to an oncogene, for example), inflammatory responses that are caused by the overexpression of certain proteins, infectious diseases, and other genetically-based disorders. Antisense technology is discussed in U.S. Pat. Nos. 5,194,428, 5,110,802 and 5,216, 141, all of which are incorporated by reference herein. Metal-free and diamagnetic metallated texaphyrin compounds, methods for making and methods for using them are described in U.S. Pat. Nos. 4,935,498, 5,162,509, 5,252,720, 5,272,142, 5,256,399, 5,292,414, and 5,369,101; and in pending applications U.S. Ser. Nos. 08/098,514, 08/100,093, now U.S. Pat. No. 5,432,171; 08/112,871, now U.S. Pat. No. 5,439,570; 08/112,786, now U.S. Pat. No. 5,475,108; 08/112,872, now U.S. Pat. No. 5,451,576, 08/135,118, now U.S. Pat. No. 5,457,183; 08/196,964; 08/227,370; 08/207, 845; 08/236,218, 08/310,501, and International No. PCT/ US94/11491; each patent and application is incorporated by reference herein. Sapphyrin compounds are disclosed in U.S. Pat. Nos. 5,041,078, 5,159,065, 5,120,411 and 5,302, 714; and in application 07/964,607; each patent and application is incorporated by reference herein.

Another embodiment of the present invention is a method for targeted intracellular DNA cleavage. The method comprises the introduction into a cell of a texaphyrin coupled to an oligonucleotide having complementary binding affinity for a targeted DNA, whereby cleavage of the targeted DNA is catalyzed by the texaphyrin upon exposure of the texaphyrin to light. The DNA may be oncogene DNA or may be normal DNA which needs to be destroyed, for example, due to improper timing of expression. The oligonucleotide coupled to the texaphyrin may be DNA, a DNA analog, or an RNA analog oligonucleotide. The texaphyrin may be a free base texaphyrin or a metallated form of texaphyrin. The metal is preferably a diamagnetic metal, most preferably Lu(III).

A further embodiment of the invention is a method of modulating the activity of a DNA, comprising contacting the DNA with a photosensitive texaphyrin either directly or in cells, tissues or bodily fluids containing the DNA, under conditions and for a time sufficient to photocleave the DNA. The texaphyrin is present in an amount effective to modulate the DNA activity or function. By "modulating the activity of a DNA" is meant that the texaphyrin interferes with or otherwise diminishes the DNA activity or function. A preferred function to be modulated is the self-replication of DNA. Another is the transcription of DNA into RNA, thereby modulating the production of a protein by an organism. Generally, the DNA selected is cell-, tissue- or disease-specific. In a presently preferred embodiment, the photosensitive texaphyrin is coupled to an oligonucleotide having complementary binding affinity for the DNA whose activity is to be modulated.

A method for inhibiting the expression of a gene in an animal comprising the administration to the animal of a texaphyrin oligonucleotide-conjugate is a further embodiment of the present invention. The oligonucleotide may have complementary binding affinity for regulatory regions of the gene or for regions encoding exons or introns. The oligonucleotide may be complementary to either strand of the DNA or to the duplex DNA. A further embodiment of the present invention is a method for inhibiting the expression of a gene in a particular tissue of an animal comprising administering to the animal a texaphyrin having specificity for the tissue. The texaphyrin may have appended an oligonucleotide complementary to the target gene.

A further embodiment of the present invention is a texaphyrin-oligonucleotide conjugate wherein two or more separate texaphyrin complexes are attached to an oligonucleotide, one at the 3', one at the 5' end, and/or one or more at an internal residue. The texaphyrin may be metal free or may be metallated. A metal ion of each of the texaphyrin complexes may be the same or it may be different. Similarly, each of the texaphyrins may be different. Use of a dual texaphyrin complex-conjugate should effect the cleavage of DNA with increased efficiency due to the concerted activity of the metal complexes. For diagnosis and treatment purposes, the administration of such a conjugate with one texaphyrin complex having a diamagnetic metal species and the other having a paramagnetic species would allow binding, imaging, and cleavage, all effected by one conjugate. In this case, binding is effected by the oligonucleotide, imaging is accomplished by MRI due to the presence of the paramagnetic metal ion, and cleavage is accomplished by the photosensitive texaphyrin containing a diamagnetic metal cation. Therefore, the biodistribution and cellular penetration of the conjugate may be determined.

Following long-standing patent law convention, the terms "a" and "an" mean "one or more" when used in this application, including the claims.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1A:
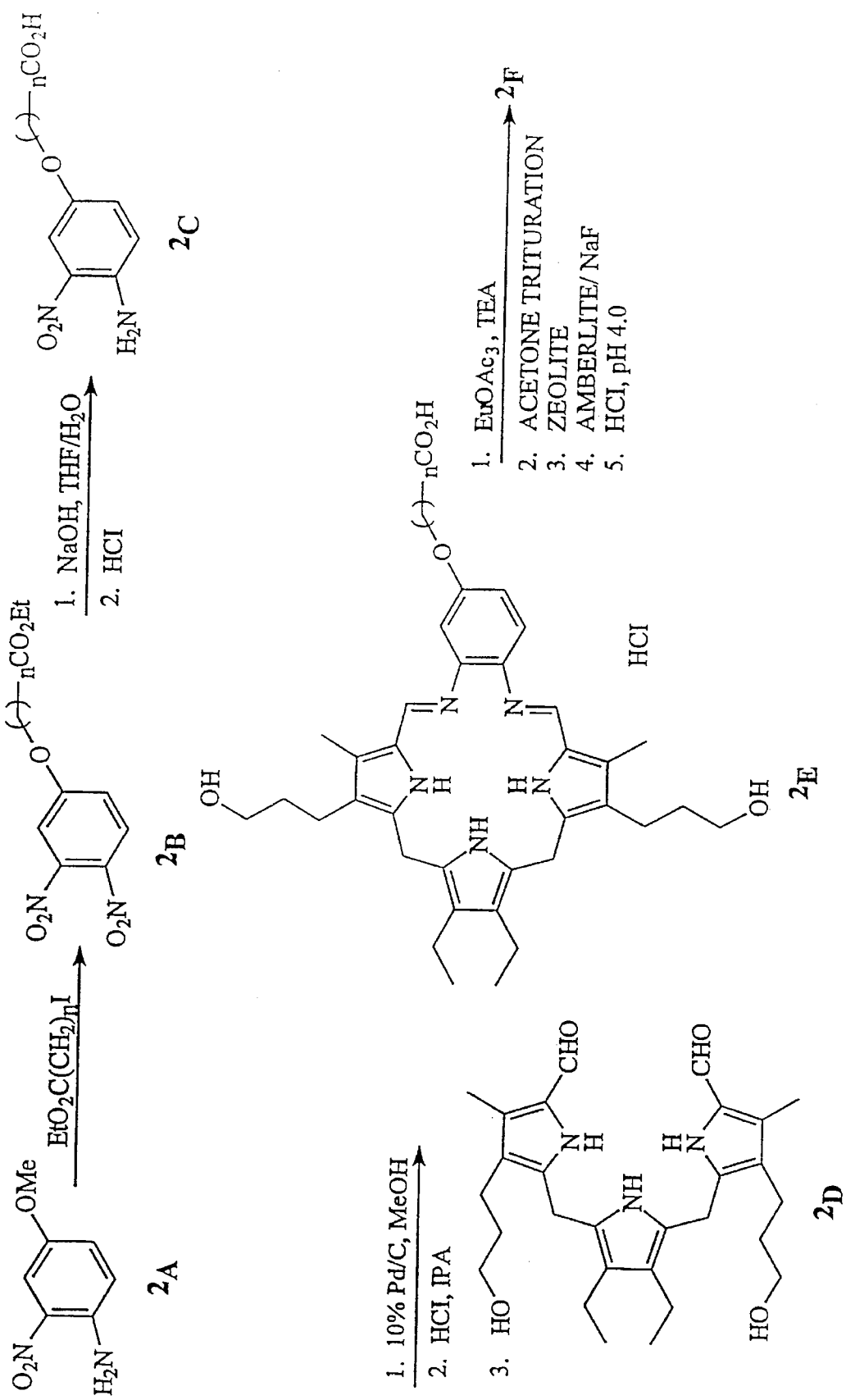
FIG. 1A and FIG. 1B schematically summarize the synthesis of an oligonucleotide conjugate of a texaphyrin metal complex, $2_H$.

The present invention involves the use of photosensitive texaphyrins for the photoinduced cleavage of a polymer of deoxyribonucleic acid. The photosensitive texaphyrin may be a free base texaphyrin or may be metallated with a diamagnetic metal.

More specifically, a photosensitive texaphyrin or texaphyrin-conjugate having catalytic activity for photolyric cleavage of DNA is contacted with the DNA polymer, and the texaphyrin is then exposed to light for a time sufficient to cleave the polymer. This reaction is carried out under conditions suitable for photocleavage of the DNA. Such time period and conditions are known to those of skill in the art or can be determined by such persons without undue experimentation. It has been found that such conditions include physiologic conditions. This is especially useful when the texaphyrin complexes are used in vivo as a treatment procedure to hydrolyze RNA, for example.

The DNA can be contacted with the texaphyrin or texaphyrin-site-directing molecule conjugate either directly, such as would be the case in certain diagnostic applications, or in cells, tissues or bodily fluids containing the DNA.

Potential particular applications for the process of this invention include antisense applications; the specific cleavage and possible subsequent recombination of DNA; destruction of viral DNA; construction of probes for controlling gene expression at the cellular level and for diagnosis; and cleavage of DNA in footprinting analyses, DNA sequencing, chromosome analyses, gene isolation, recombinant DNA manipulations, mapping of large genomes and chromosomes, in chemotherapy and in site-directing mutagenesis.

In the practice of the present invention, the texaphyrin may be chosen from any texaphyrin molecule, including those now known and disclosed in the U.S. patents and patent applications incorporated by reference herein. Representatives of texaphyrins included within the present invention are encompassed within the following structure I:

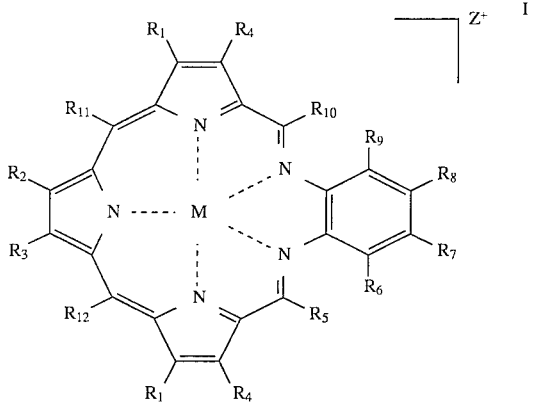

In this texaphyrin complex, M is H or a diamagnetic metal cation.

$R_1$–$R$ , $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamide, carboxyamidealkyl, aminoalkyl, sulfonatoalkyl, amidealkyl, aryl, a site-directing molecule, a catalytic group, or a couple to a site-directing molecule or to a catalytic group.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple to a saccharide, to a site-directing molecule or to a catalytic group.

Z will typically be an integer less than or equal to 5. In the context of the basic macrocycle with a divalent or trivalent metal cation, Z is 1 or 2; however, one skilled in the art in light of the present disclosure would realize that the complexes described in the present invention may have one or more additional ligands providing charge neutralization and/ or coordinative saturation to the metal ion. Such ligands include chloride, nitrate, acetate, and hydroxide, among others. The value of Z would also be altered due to charges present on, for example, a covalently attached site-directing molecule, such as charges of the phosphate groups on an oligonucleotide.

In a preferred embodiment, at least one of $R_1$–$R_{12}$ is a site-directing molecule or is a couple to a site-directing molecule. For bulky R groups on the benzene ring portion of the molecule such as antibodies, peptides or oligonucleotides, one skilled in the art would realize that derivatization at one position on the benzene portion is more preferred.

"Alkyl" means alkyl groups, straight, branched or as cyclic isomers, with generally one to fifty, preferably one to thirty, more preferably one to ten, carbon atoms.

"Alkenyl" means alkenyl groups, straight, branched or as cyclic isomers, with generally two to fifty, preferably two to thirty, more preferably two to ten, carbon atoms, and with one to five or more double bonds, preferably one to five, more preferably one to three double bonds.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$alkyls being preferred, and diols of $C_{1-3}$alkyls being more preferred; and polyethylene glycol, polypropylene glycol and polybutylene glycol as well as polyalkylene glycols containing combinations of ethylene, propylene and butylene.

"Oxyalkyl" means alkyl groups as herein described with oxygen atoms, including ether or ester linkages. The number of repeating oxyalkyls within a substituent may be up to 200, preferably from 1 to 20, more preferably from 1 to 7, and most preferably is 2–3.

"Hydroxyalkoxy" means alkyl groups as described herein having ether or ester linkages, as well as hydroxyl groups, substituted hydroxyl groups, carboxyl groups, substituted carboxyl groups or the like.

"Carboxy" groups include carboxylic acids of the alkyls described herein as well as aryl carboxylic acids such as benzoic acid. "Carboxyalkyl" means alkyl groups having hydroxyl groups, carboxyl or amide substituted ethers, ester linkages, tertiary amide linkages removed from the ether or the like. Representative examples of "carboxyamides" include primary carboxyamides ($CONH_2$), and secondary (CONHR') and tertiary (CONR'R") carboxyamides where each of R' and R" is a functional group as described herein. "Carboxyamidealkyl" means alkyl groups with hydroxyl groups, secondary or tertiary amide linkages or the like.

Representatives of useful amines include a primary, secondary or tertiary amine of an alkyl as described hereinabove.

"Aryl" may be a phenyl group, unsubstituted or substituted with a nitro, carboxy, sulfonic acid, hydroxy, oxyalkyl, or halide.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides; as well as open chain forms of various sugars, and the like. Examples of amine-derivatized sugars are galactosamine, glucosamine, and sialic acid.

"Carboxyamidealkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether, or the like.

For the above-described texaphyrins, hydroxyalkoxy may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to ((2n+1)–2x). The hydroxyalkoxy or saccharide may be $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than ((2n+1)–q), q is zero or a positive integer less than or equal to 2n+1, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to ((2m+1)–2w), and R is H, alkyl, hydroxyalkyl, or $C_mH_{((2m+1)-r)}O_zR^b_r$ where m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, $N(R)OCC_{(m-w)}H_{((2m+1)-2w)}O_wO_z$, or a site-directing molecule or catalytic group. In this case, m is a positive integer from 1 to 10, w is zero or a positive integer less than or equal to m, z is zero or a positive integer less than or equal to ((2m+1)–2w), and R is H, alkyl, hydroxyalkyl, or $C_mH_{((2m+1)-r)}O_zR^b_r$. In this case, m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide. In a preferred embodiment, $R^a$ is an oligonucleotide.

Carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than ((2n+1)–q), q is zero or a positive integer less than or equal to 2n+1, and $R^c$ is $(CH_2)_nCO_2R^d$, $(CH_2)_nCONHR^d$, $(CH_2)_nCON(R^d)_2$ or a site-directing molecule or catalytic group. In this case, n is a positive integer from 1 to 10, $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to ((2m+1)–2w), and R is H, alkyl, hydroxyalkyl, or $C_mH_{((2m+1)-r)}O_zR^b_r$. In this case, m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide. In a preferred embodiment, $R^c$ is an oligonucleotide.

The term "catalytic group" means a chemical functional group that assists catalysis by acting as a general acid, Brønsted acid, general base, Brønsted base, nucleophile, or any other means by which the activation barrier to reaction is lowered or the ground state energy of the substrate is increased. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, $(LysAla)_n$, $(LysLeuAla)_n$ where n is from 1–30 or preferably 1–10 or more preferably 2–7 and the like; derivatives thereof; and metallotexaphyrin complexes. The term "appended to the texaphyrin complex-site directed molecule conjugate" means that the catalytic groups are attached either directly to the metallotexaphyrin complex or to the texaphyrin complex via a linker or couple of variable length, or are attached to the site-directing molecule portion of a texaphyrin complex-conjugate either with or without a linker or couple of variable length.

Exemplary site-directing molecules useful herein include, but are not limited to, polydeoxyribonucleotides, oligodeoxyribonucleotides, polyribonucleotide analogs, oligoribonucleotide analogs, polyamides including peptides having affinity for a biological receptor and proteins such as antibodies, steroids and steroid derivatives, hormones such as estradiol or histamine, hormone mimics such as morphine, and further macrocycles such as sapphyrins and rubyrins.

The oligonucleotides may be derivatized at the bases, the sugars, the ends of the chains, or at the phosphate groups of the backbone to promote in vivo stability. Modifications of the phosphate groups are preferred in one embodiment since phosphate linkages are sensitive to nuclease activity. Presently preferred derivatives are the methylphosphonates, phosphotriesters, phosphorothioates, and phosphormidates. Additionally, the phosphate linkages may be completely substituted with non-phosphate linkages such as amide linkages. Appendages to the ends of the oligonucleotide chains also provide exonuclease resistance. Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy or propoxy. The alkenyl group is preferably allyl. The alkyl group is preferably a methyl group and the methyl group is attached to the 2' oxygen of the ribose. Other alkyl groups may be ethyl or propyl.

It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates and phosphoramidates and the like. Deoxyribonucleotides, deoxyribonucleotide analogs and ribonucleotide analogs are contemplated as site-directing molecules in the present invention.

The term "texaphyrin-oligonucleotide conjugate" means that an oligonucleotide is attached to the texaphyrin in a 5' or a 3' linkage, or in both types of linkages to allow the texaphyrin to be an internal residue in the conjugate. It can also refer to a texaphyrin that is linked to an internal base of the oligonucleotide. The oligonucleotide or other site-directing molecule may be attached either directly to the texaphyrin or to the texaphyrin via a linker or a couple of variable length. During catalysis, for example, the texaphyrin portion of a texaphyrin-oligonucleotide conjugate is placed in the vicinity of the substrate upon binding of the oligonucelotide to the targeted nucleic acid substrate.

A conjugate group having site specificity or catalytic activity may be covalently coupled to a texaphyrin directly on the macrocycle ring or through various couples. A couple may be described as a linker, i.e., the covalent product formed by reaction of a reactive group designed to attach covalently another molecule at a distance from the texaphyrin macrocycle. Exemplary linkers or couples are amides, amine, thiol, thioether, ether, or phosphate covalent bonds as described in the examples for attachment of oligonucleotides. In preferred embodiments, conjugates and appended groups are covalently bonded to the texaphyrin via a carbon-carbon, a carbon-nitrogen, a carbon-sulfur, or a carbon-oxygen bond, more preferred being a carbon-oxygen or a carbon-nitrogen bond.

In an embodiment of the present invention, M may be a diamagnetic metal cation, and preferably is selected from the group consisting of $Zn^{+2}$, $Cd^{+2}$, $Y^{+3}$, $In^{+3}$, and lanthanides.

In presently preferred texaphyrins, $R_1$ is hydroxyalkyl and $R_2$, $R_3$ and $R_4$ are alkyl. Alternatively, $R_3$ may be a site-directing molecule or a couple to a site-directing molecule, preferably an oligonucleotide or a couple to an oligonucleotide. In a further presently preferred texaphyrin, $R_1$ is $CH_2CH_3$ or $(CH_2)_2CH_2OH$, $R_2$ and $R_3$ are $CH_2CH_3$, $R_4$ is $CH_3$, and $R_7$ and $R_8$ are $OCH_2CH_2CH_2OH$ or $R_7$ and $R_8$ are $O(CH_2CH_2O)_tCH_2CH_2OR'$ where t is 0–200, preferably 2–100, and R' is H or $CH_3$. Alternatively, $R_7$ is a site-directing molecule or a couple thereto, preferably an oligonucleotide or a couple thereto, more preferably $O(CH_2)_nCO$-oligonucleotide where n is 1–7 and preferably 1–3; and $R_8$ is H, $CH_3$ or $OCH_3$. In a further presently preferred embodiment, $R_1$ is $CH_2CH_3$ or $(CH_2)_2CH_2OH$, $R_2$ and $R_3$ are $CH_2CH_3$, $R_4$ is $CH_3$, $R_7$ is $O(CH_2CH_2O)_tCH_2CH_2OR'$ where t is 0–200, preferably 2–100, and R' is H or $CH_3$, and $R_8$ is a site-directing molecule or a couple thereto, preferably an oligonucleotide or a couple thereto, more preferably $O(CH_2)_nCO$-oligonucleotide where n is 1–7 and preferably 1–3.

In a further embodiment of the present invention, at least one of $R_1$–$R_{12}$ is a site-directing molecule or is a couple to a site-directing molecule. In a more preferred embodiment, the site-directing molecule is an oligonucleotide or is a couple to an oligonucleotide and most preferably, the oligonucleotide is a deoxyribonucleotide or a 2'-O-alkyl ribonucleotide. The oligonucleotide has complementary binding affinity for the DNA in a region proximal to the site of desired cleavage. The oligonucleotide may have complementary binding affinity for viral DNA, thereby cleaving the viral DNA and killing the organism. The oligonucleotide may be a deoxyribonucleotide and have complementary binding affinity for oncogenes. The site-directing molecule may have binding specificity for localization to a treatment site and the biological receptor may be localized to a treatment site.

Water-soluble texaphyrins are often preferred for the applications described herein, particularly when in vivo administration and treatment are contemplated. "Water-soluble" means soluble in aqueous fluids to about 1 mM or better. Such characteristics allow these texaphyrins to be useful in a biological environment. Improved water solubility can be achieved by, for example, substituents chosen from saccharides or hydroxylated substituents.

While all of the above-described texaphyrins are presently preferred compounds, the invention is not limited thereto and any photosensitive texaphyrin having catalytic activity for light-induced cleavage of DNA may be useful in the practice of the invention.

An individual skilled in the art of organic synthesis in light of the present disclosure is able to prepare a large variety of texaphyrins and metallotexaphyrin complexes which are expected to photolytically cleave DNA, an important biological species.

Texaphyrin compounds and methods for making are described in the patent and applications previously listed herein and in International publication WO 94/29316, each of which is incorporated by reference herein.

Generally, the introduction of hydroxy substituents on the B (benzene ring) portion of the texaphyrin molecule is accomplished by their attachment to phenylenediamine in the 4 and 5 positions of the phenyl subunit of the molecule or they may be added in a synthetic step following the condensation step that forms the macrocycle metal complex as described in the above-named patents. The introduction of hydroxy substituents on the T (tripyrrole or tripyrrane) portion of the molecule is accomplished by appropriate functionalization of the alkyl substituents in the 3 and/or 4 positions of the pyrrole rings at a synthetic step prior to condensation with the substituted phenylenediamine. Standard deprotection methodology such as ester hydrolysis may be used to unmask free hydroxyl substituents. Alternatively, they may be prepared as the result of ester reduction. These derivatives exhibit significant solubility in aqueous media, up to 1 mM or better, yet they retain affinity for lipid-rich regions which allows them to be useful in biological environments.

One skilled in the art of organic synthesis in light of the present disclosure and the disclosures in the patents, applications and publications incorporated by reference herein could extend and refine the basic synthetic chemistry to produce texaphyrins having various substituents. For example, a doubly carboxylated texaphyrin in which the carboxyl groups are linked to the texaphyrin core via aryl ethers or functionalized alkyl substituents could be converted to various esterified products wherein the ester linkages serve to append further hydroxyl-containing substituents. Polyhydroxylated texaphyrin derivatives may be synthesized via the use of secondary amide linkages. Saccharide moieties may be appended via amide bonds. Polyhydroxylated texaphyrin derivatives containing branched polyhydroxyl (polyol) subunits may be appended to the texaphyrin core via aryl ethers or ester linkages.

Treatment of carboxylated texaphyrins with thionyl chloride or p-nitrophenol acetate would generate activated acyl species suitable for attachment to monoclonal antibodies or other biomolecules of interest. Standard in situ coupling methods (e.g., 1,1'-carbonyldiimidazole) could be used to effect the conjugation.

The selectivity of the texaphyrins may be enhanced by covalently linking oligonucleotides onto the periphery of the macrocycle. Amides, ethers and thioethers are representative of linkages which may be used for this purpose. Oligonucleotides functionalized with amines at the 5'-end, the 3'-end, or internally at sugar or base residues may be modified post-synthetically with an activated carboxylic ester derivative of the texaphyrin complex. Alternatively, oligonucleotide analogs containing one or more thiophosphate or thiol groups may be selectively alkylated at the sulfur atom(s) with an alkyl halide derivative of the texaphyrin complex. The resultant oligonucleotide-complex conjugates may be designed so as to provide optimal catalytic interaction between a target nucleic acid and the bound texaphyrin. The oligonucleotide may be large enough to bind probably at least about 9–12 nucleotides of complementary nucleic acid. Specific methods for preparing texaphyrin-oligonucleotide conjugates are disclosed in WO 94/29316, incorporated herein by reference.

The use of texaphyrins to photolytically cleave DNA in vivo as a treatment procedure relies on the effective localization of the complex to the site of desired cleavage. A site of desired cleavage may be a position novel to undesired organisms in terms of health care. A site of desired cleavage may be an DNA encoding a product deleterious to the host or may be a normal DNA that is deleterious in some way.

Treating native DNA with the texaphyrin complexes in a site-specific manner results in the texaphyrin complex binding to a complementary DNA sequence via an appended oligonucleotide. The texaphyrin complex then cleaves the RDA proximal to this specific site.

Texaphyrin-oligonucleotide conjugates may be developed into antisense reagents useful in the present invention. This antisense strategy provides a clear and rational method for new drug design because there is one requirement, namely that the antisense probe hybridize to its target molecule. The hybridization requirement is very well understood via complementary Watson-Crick or Hoogsteen base pairing. Unlike the present methods in the art which require screening of thousands of compounds and X-ray crystal structure analysis, the information needed for antisense technology is the sequence of the target. Treating single-stranded native DNA, such as viral DNA, with a texaphyrin-oligonucleotide conjugate results in the conjugate binding to a complementary DNA sequence via the appended oligonucleotide. The texaphyrin complex then photocleaves the DNA proximal to this specific binding site when the texaphyrin is exposed to light. The texaphyrin complex enhances the therapeutic activity of the antisense oligonucleotide, not only by facilitating cellular uptake of the oligonucleotide but also by cleaving the target DNA within the cell independent of RNase H. Additionally, attachment to the texaphyrin complex causes the oligonucleotide antisense agent to take on some of the pharmacodynamic and biodistribution properties of the texaphyrin such as selective localization in tumors.

The texaphyrin-oligonucleotide conjugates will be useful for inhibiting the expression of a gene in an animal or in a particular tissue of an animal. They are also useful in a method for targeted intracellular DNA photocleavage.

Texaphyrins are ideal for intracellular transport and cell delivery of a large variety of monomeric and oligomeric nucleotide species and their derivatives, including RNA, DNA, anti-viral agents and antisense agents. Texaphyrins exhibit the ability to cross cellular membranes. When the texaphyrin is complexed or conjugated to a second molecule, the second molecule, in the present case an oligonucleotide, will be transported across the membrane and into the cell together with the texaphyrin.

The present method of photolyric cleavage would have immediate applications for anti-viral therapy as well as for cancers (an oligonucleotide complementary to an oncogene, for example), inflammatory responses that are caused by the overexpression of certain proteins, infectious diseases, and other genetically based disorders.

Exemplary texaphyrins useful in the present invention are listed in Tables A–C, see below.

Unless defined otherwise, all technical and scientific terms used herein have the same meaning as commonly understood by one of ordinary skill in the art to which this invention belongs.

In a preferred embodiment, the invention involves the site-specific cleavage of a polymer of deoxyribonucleic acid using a photosensitive texaphyrin-oligonucleotide conjugate where the oligonucleotide is a site-directing molecule having sequence complementarity to a portion of the DNA to be cleaved. Preferred is a metallotexaphyrin where the metal is a diamagnetic metal, more preferably the diamagnetic metal is Lu(III), La(III), In(III), Y(III), Zn(II), or Cd(II), and a most preferred diamagnetic metal is Lu(III).

An individual skilled in the art of organic synthesis in light of the present disclosure is able to prepare a large variety of photosensitive texaphyrins, all of which are expected to cleave DNA, an important biological species.

TABLE A

Representative Substituents for Texaphyrin Macrocycles A1–A50 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2CH_3$ | $CH_2CH_3$ | $CH_3$ | H | COOH |
| A2 | $CH_2(CH_2)_2OH$ | $CH_2CH_3$ | $CH_2CH_3$ | $CH_3$ | H | COOH |
| A3 | $CH_2(CH_2)_2OH$ | $CH_2CH_3$ | $CH_2CH_3$ | $CH_3$ | H | CONHCH—$(CH_2OH)_2$ |
| A4 | $CH_2(CH_2)_2OH$ | $CH_2CH_3$ | $CH_2CH_3$ | $CH_3$ | H | CONHCH—$(CH_2OH)_2$ |
| A5 | $CH_2(CH_2)_2OH$ | $CH_2CH_3$ | $CH_2CH_3$ | $CH_3$ | H | H |
| A6 | $CH_2(CH_2)_2OH$ | $CH_2CH_3$ | $CH_2CH_3$ | $CH_3$ | H | $OCH_3$ |
| A7 | $CH_2(CH_2)_2OH$ | $CH_2CH_3$ | $CH_2CH_3$ | $CH_3$ | H | $OCH_3$ |
| A8 | $CH_2(CH_2)_2OH$ | $CH_2CH_3$ | $CH_2CH_3$ | $CH_3$ | H | $OCH_3$ |
| A9 | $CH_2(CH_2)_2OH$ | $CH_2CH_3$ | $CH_2CH_3$ | $CH_3$ | H | $OCH_3$ |
| A10 | $CH_2(CH_2)_2OH$ | $CH_2CH_3$ | $CH_2CH_3$ | $CH_3$ | H | $OCH_3$ |
| A11 | $CH_2(CH_2)_2OH$ | $CH_2CH_3$ | $CH_2CH_3$ | $CH_3$ | H | $OCH_3$ |
| A12 | $CH_2(CH_2)_2OH$ | $CH_2CH_3$ | $CH_2CH_3$ | $CH_3$ | H | $OCH_3$ |
| A13 | $CH_2(CH_2)_2OH$ | $CH_2CH_3$ | $CH_2CH_3$ | $CH_3$ | H | $CH_3$ |
| A14 | $CH_2(CH_2)_2OH$ | $CH_2CH_3$ | $CH_2CH_3$ | $CH_3$ | H | $CH_3$ |
| A15 | $CH_2(CH_2)_2OH$ | $CH_2CH_3$ | $CH_2CH_3$ | $CH_3$ | H | $CH_3$ |
| A16 | $CH_2(CH_2)_2OH$ | $CH_2CH_3$ | $CH_2CH_3$ | $CH_3$ | H | $CH_3$ |
| A17 | $CH_2(CH_2)_2OH$ | $CH_2CH_3$ | $CH_2CH_3$ | $CH_3$ | $CH_3$ | H |
| A18 | $CH_2(CH_2)_2OH$ | $CH_2CH_3$ | $CH_2CH_3$ | $CH_3$ | $CH_3$ | H |
| A19 | $CH_2(CH_2)_2OH$ | $CH_2CH_3$ | $CH_2CH_3$ | $CH_3$ | $CH_3$ | H |
| A20 | $CH_2(CH_2)_2OH$ | $CH_2CH_3$ | $CH_2CH_3$ | $CH_3$ | $CH_3$ | H |
| A21 | $CH_2(CH_2)_2OH$ | $CH_2CH_3$ | $CH_2CH_3$ | $CH_3$ | $CH_3$ | H |
| A22 | $CH_2(CH_2)_2OH$ | $CH_2CH_3$ | $CH_2CH_3$ | $CH_3$ | $CH_3$ | H |
| A23 | $CH_2(CH_2)_2OH$ | $CH_2CH_3$ | $CH_2CH_3$ | $CH_3$ | $CH_3$ | H |
| A24 | $CH_2(CH_2)_2OH$ | $CH_2CH_3$ | $CH_2CH_3$ | $CH_3$ | $CH_3$ | H |
| A25 | $CH_2(CH_2)_2OH$ | $CH_2CH_3$ | $CH_2CH_3$ | $CH_3$ | $CH_3$ | H |
| A26 | $CH_2(CH_2)_2OH$ | $CH_2CH_3$ | $CH_2CH_3$ | $CH_3$ | $CH_3$ | OH |
| A27 | $CH_2(CH_2)_2OH$ | $CH_2CH_3$ | $CH_2CH_3$ | $CH_3$ | $CH_3$ | F |
| A28 | $CH_2(CH_2)_2OH$ | $CH_2CH_3$ | $CH_2CH_3$ | $CH_3$ | $CH_2(CH_2)_6OH$ | H |
| A29 | $CH_2(CH_2)_2OH$ | $CH_2CH_3$ | $CH_2CH_3$ | $CH_3$ | H | Br |
| A30 | $CH_2(CH_2)_2OH$ | $CH_2CH_3$ | $CH_2CH_3$ | $CH_3$ | H | $NO_2$ |

TABLE A-continued

Representative Substituents for Texaphyrin Macrocycles A1–A50 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A31 | $CH_2(CH_2)_2OH$ | $CH_2CH_3$ | $CH_2CH_3$ | $CH_3$ | H | COOH |
| A32 | $CH_2(CH_2)_2OH$ | $CH_2CH_3$ | $CH_2CH_3$ | $CH_3$ | H | $CH_3$ |
| A33 | $CH_2(CH_2)_2OH$ | $CH_2CH_3$ | $CH_2CH_3$ | $CH_3$ | $C_6H_5$ | H |
| A34 | $CH_2(CH_2)_2OH$ | COOH | COOH | $CH_3$ | $CH_2CH_3$ | H |
| A35 | $CH_2(CH_2)_2OH$ | $COOCH_2CH_3$ | $COOCH_2CH_3$ | $CH_3$ | $CH_3$ | H |
| A36 | $CH_2CH_2CON(CH_2CH_2OH)_2$ | $CH_2CH_3$ | $CH_2CH_3$ | $CH_3$ | $CH_3$ | H |
| A37 | $CH_2CH_2ON(CH_3)CH_2$-$(CHOH)_4CH_2OH$ | $CH_2CH_3$ | $CH_2CH_3$ | $CH_3$ | $CH_3$ | H |
| A38 | $CH_2CH_3$ | $CH_2CH_3$ | $CH_2CH_3$ | $CH_3$ | $CH_2(CH_2)_6OH$ | H |
| A39 | $CH_2(CH_2)_2OH$ | $CH_2CH_3$ | $CH_2CH_3$ | $CH_3$ | $CH_3$ or $CH_2CH_3$ | H |
| A40 | $CH_2(CH_2)_2OH$ | $CH_2CH_3$ | $CH_2CH_3$ | $CH_3$ | $CH_3$ or $CH_2CH_3$ | H |
| A41 | $CH_2(CH_2)_2OH$ | $CH_2CH_3$ | $CH_2CH_3$ | $CH_3$ | $CH_3$ or $CH_2CH_3$ | H |
| A42 | $CH_2(CH_2)_2OH$ | $CH_2CH_3$ | $CH_2CH_3$ | $CH_3$ | $CH_3$ or $CH_2CH_3$ | H |
| A43 | $CH_2(CH_2)_2OH$ | $CH_2CH_3$ | $CH_2CH_3$ | $CH_3$ | $CH_3$ or $CH_2CH_3$ | H |
| A44 | $CH_2(CH_2)_2OH$ | $CH_2CH_3$ | $CH_2CH_3$ | $CH_3$ | $CH_3$ or $CH_2CH_3$ | H |
| A45 | $CH_2(CH_2)_2OH$ | $CH_2CH_3$ | $CH_2CH_3$ | $CH_3$ | $CH_3$ or $CH_2CH_3$ | H |
| A46 | $CH_2(CH_2)_2OH$ | $CH_2CH_3$ | $CH_2CH_3$ | $CH_3$ | $CH_3$ or $CH_2CH_3$ | H |
| A47 | $CH_2(CH_2)_2OH$ | $CH_2CH_3$ | $CH_2CH_3$ | $CH_3$ | $CH_3$ or $CH_2CH_3$ | H |
| A48 | $CH_2(CH_2)_2OH$ | $CH_2CH_3$ | $CH_2CH_3$ | $CH_3$ | $CH_3$ or $CH_2CH_3$ | H |
| A49 | $CH_2(CH_2)_2OH$ | $CH_2CH_3$ | $CH_2CH_3$ | $CH_3$ | $CH_3$ or $CH_2CH_3$ | H |
| A50 | $CH_2(CH_2)_2OH$ | $CH_2CH_3$ | $CH_2CH_3$ | $CH_3$ | $CH_3$ or $CH_2CH_3$ | H |
| A51 | $CH_2(CH_2)_2OH$ | $CH_2CH_3$ | $CH_2CH_3$ | $CH_3$ | H | H |
| A52 | $CH_2(CH_2)_2OH$ | $CH_2CH_3$ | $CH_2CH_3$ | $CH_3$ | H | H |
| A53 | $CH_2(CH_2)_2OH$ | $CH_2CH_3$ | $CH_2CH_3$ | $CH_3$ | H | H |
| A54 | $CH_2(CH_2)_2OH$ | $CH_2CH_3$ | $CH_2CH_3$ | $CH_3$ | H | H |
| A55 | $CH_2(CH_2)_2OH$ | $CH_2CH_3$ | $CH_2CH_3$ | $CH_3$ | $CH_3$ or $CH_2CH_3$ | H |
| A56 | $CH_2(CH_2)_2OH$ | $CH_2CH_3$ | $CH_2CH_3$ | $CH_3$ | $CH_3$ or $CH_2CH_3$ | H |

TABLE B

Representative Substituents for Texaphyrin Macrocycles A1–A50 of the Present Invention.
Substituents for $R_1$–$R_6$ Are Provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A1 | $O(CH_2)_3OH$ | $O(CH_2)_3OH$ | $O(CH_2)_3OH$ | H | H | H |
| A2 | $O(CH_2CH_2O)_3CH_3$ | $O(CH_2CH_2O)_3CH_3$ | COOH | H | H | H |
| A3 | $O(CH_2CH_2O)_3CH_3$ | $O(CH_2CH_2O)_3CH_3$ | O-saccharide | H | H | H |
| A4 | $O(CH_2CH_2O)_3CH_3$ | $O(CH_2CH_2O)_3CH_3$ | $O(CH_2CH_2O)_3CH_3$ | H | H | H |
| A5 | $O(CH_2CH_2O)_3CH_3$ | $O(CH_2)_3CON$-linker-oligo | $O(CH_2CH_2O)_3CH_3$ | H | H | H |
| A6 | H | $OCH_2CON$-linker-oligo | $OCH_3$ | H | H | H |
| A7 | H | $OCH_2CO$-poly-L-lysine | $OCH_3$ | H | H | H |
| A8 | H | $OCH_2CO$-estradiol | $OCH_3$ | H | H | H |
| A9 | H | $O(CH_2CH_2O)_3CH_3$ | $OCH_3$ | H | H | H |
| A10 | $O(CH_2CH_2O)_3CH_3$ | $O(CH_2CH_2O)_3CH_3$ | $OCH_3$ | H | H | H |
| A11 | $O(CH_2CH_2O)_3CH_3$ | $OCH_2CON$-linker-oligo | $OCH_3$ | H | H | H |
| A12 | $O(CH_2CH_2O)_3CH_3$ | $OCH_2CO$-estradiol | $OCH_3$ | H | H | H |
| A13 | $O(CH_2CH_2O)_3CH_3$ | $O(CH_2CH_2O)_3CH_3$ | $O(CH_2CH_2O)_3CH_3$ | H | H | H |
| A14 | $O(CH_2CH_2O)_3CH_3$ | $OCH_2CO$-estradiol | $O(CH_2CH_2O)_3CH_3$ | H | H | H |
| A15 | $O(CH_2CH_2O)_3CH_3$ | $O(CH_2CH_2O)_{120}CH_3$ | $OCH_3$ | H | H | H |
| A16 | H | saccharide | $OCH_3$ | H | H | H |
| A17 | $O(CH_2)_3OH$ | $O(CH_2)_3OH$ | H | $CH_3$ | H | H |
| A18 | H | $O(CH_2CH_2O)_3CH_3$ | H | $CH_3$ | H | H |
| A19 | $O(CH_2CH_2O)_3CH_3$ | $O(CH_2CH_2O)_3CH_3$ | H | $CH_3$ | H | H |
| A20 | H | $OCH_2CON$-linker-oligo | H | $CH_3$ | H | H |
| A21 | H | $OCH_2CO$-estradiol | H | $CH_3$ | H | H |
| A22 | H | $OCH_2CON(CH_2CH_2OH)_2$ | H | $CH_3$ | H | H |
| A23 | $O(CH_2CH_2O)_3CH_3$ | $O(CH_2CH_2O)_{120}CH_3$ | H | $CH_3$ | H | H |

TABLE B-continued

Representative Substituents for Texaphyrin Macrocycles A1–A50 of the Present Invention.
Substituents for $R_1$–$R_6$ Are Provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A24 | $O(CH_2CH_2O)_3CH_3$ | $OCH_2CON$-linker-oligo | H | $CH_3$ | H | H |
| A25 | H | $CH_2CON(CH_3)CH_2$—$(CHOH)_4CH_2OH$ | H | $CH_3$ | H | H |
| A26 | $O(CH_2CH_2O)_3CH_3$ | $O(CH_2CH_2O)_3CH_3$ | OH | $CH_3$ | H | H |
| A27 | $O(CH_2CH_2O)_3CH_3$ | $O(CH_2CH_2O)_3CH_3$ | F | $CH_3$ | H | H |
| A28 | $O(CH_2CH_2O)_3CH_3$ | $O(CH_2CH_2O)_3CH_3$ | H | $CH_2(CH_2)_6OH$ | H | H |
| A29 | $O(CH_2CH_2O)_3CH_3$ | $O(CH_2CH_2O)_3CH_3$ | Br | H | H | H |
| A30 | $O(CH_2CH_2O)_3CH_3$ | $O(CH_2CH_2O)_3CH_3$ | $NO_2$ | H | H | H |
| A31 | $O(CH_2CH_2O)_3CH_3$ | $O(CH_2CH_2O)_3CH_3$ | COOH | H | H | H |
| A32 | $O(CH_2CH_2O)_3CH_3$ | $O(CH_2CH_2O)_3CH_3$ | $CH_3$ | H | H | H |
| A33 | $O(CH_2CH_2O)_3CH_3$ | $O(CH_2CH_2O)_3CH_3$ | H | $C_6H_5$ | H | H |
| A34 | $O(CH_2CH_2O)_3CH_3$ | $O(CH_2CH_2O)_3CH_3$ | H | $CH_2CH_3$ | H | H |
| A35 | $O(CH_2CH_2O)_3CH_3$ | $O(CH_2CH_2O)_3CH_3$ | H | $CH_3$ | H | H |
| A36 | $O(CH_2CH_2O)_3CH_3$ | $O(CH_2CH_2O)_3CH_3$ | H | $CH_3$ | H | H |
| A37 | $OCH_3$ | $OCH_3$ | H | $CH_3$ | H | H |
| A38 | H | $OCH_2CO_2$-glucosamine | H | $CH_2(CH_2)_6OH$ | H | H |
| A39 | $O(CH_2)_3OH$ | $O(CH_2)_3OH$ | H | $CH_3$ or $CH_2CH_3$ | $CH_3$ or $CH_2CH_3$ | $CH_3$ or $CH_2CH_3$ |
| A40 | $O(CH_2CH_2O)_3CH_3$ | $O(CH_2CH_2O)_3CH_3$ | H | $CH_3$ or $CH_2CH_3$ | $CH_3$ or $CH_2CH_3$ | $CH_3$ or $CH_2CH_3$ |
| A41 | $O(CH_2)_3OH$ | $O(CH_2CH_2O)_3CH_3$ | H | $CH_3$ or $CH_2CH_3$ | $CH_3$ or $CH_2CH_3$ | $CH_3$ or $CH_2CH_3$ |
| A42 | H | $O(CH_2)_nCON$-linker-oligo, n = 1,2,3 | H $CH_2CH_3$ | $CH_3$ or $CH_2CH_3$ | $CH_3$ or $CH_2CH_3$ | $CH_3$ or $CH_2CH_3$ |
| A43 | H | $O(CH_2)_nCO$-estradiol, n = 1,2,3 | H $CH_2CH_3$ | $CH_3$ or $CH_2CH_3$ | $CH_3$ or $CH_2CH_3$ | $CH_3$ or |
| A44 | H | saccharide | H | $CH_3$ or $CH_2CH_3$ | $CH_3$ or $CH_2CH_3$ | $CH_3$ or $CH_2CH_3$ |
| A45 | $O(CH_2)_3OH$ | $O(CH_2)_nCON$-linker-oligo, n = 1,2,3 | H $CH_2CH_3$ | $CH_3$ or $CH_2CH_3$ | $CH_3$ or $CH_2CH_3$ | $CH_3$ or |
| A46 | $O(CH_2)_3OH$ | $O(CH_2)_nCO$-estradiol, n = 1,2,3 | H $CH_2CH_3$ | $CH_3$ or $CH_2CH_3$ | $CH_3$ or $CH_2CH_3$ | $CH_3$ or |
| A47 | $O(CH_2)_3OH$ | saccharide | H | $CH_3$ or $CH_2CH_3$ | $CH_3$ or $CH_2CH_3$ | $CH_3$ or $CH_2CH_3$ |
| A48 | $O(CH_2CH_2O)_3CH_3$ | $O(CH_2)_nCON$-linker-oligo, n = 1,2,3 | H $CH_2CH_3$ | $CH_3$ or $CH_2CH_3$ | $CH_3$ or $CH_2CH_3$ | $CH_3$ or |
| A49 | $O(CH_2CH_2O)_3CH_3$ | $O(CH_2)_nCO$-estradiol, n = 1,2,3 | H $CH_2CH_3$ | $CH_3$ or $CH_2CH_3$ | $CH_3$ or $CH_2CH_3$ | $CH_3$ or |
| A50 | $O(CH_2CH_2O)_3CH_3$ | saccharide | H | $CH_3$ or $CH_2CH_3$ | $CH_3$ or $CH_2CH_3$ | $CH_3$ or $CH_2CH_3$ |
| A51 | $O(CH_2CH_2O)_3CH_3$ | $O(CH_2)_nCON$-linker-oligo, n = 1,2,3 | H | H $CH_2CH_3$ | $CH_3$ or $CH_2CH_3$ | $CH_3$ or |
| A52 | $O(CH_2CH_2O)_3CH_3$ | $O(CH_2CH_2O)_3CH_3$ | H | H | $CH_3$ or $CH_2CH_3$ | $CH_3$ or $CH_2CH_3$ |
| A53 | $O(CH_2CH_2O)_3CH_3$ | $O(CH_2CH_2O)_3CH_3$ | H | H | $CH_2(CH_2)_2OH$ | $CH_2(CH_2)_2OH$ |
| A54 | $O(CH_2CH_2O)_3CH_3$ | $O(CH_2)_nCON$-linker-oligo n = 1,2,3 | H | H | $CH_2(CH_2)_2OH$ | $CH_2(CH_2)_2OH$ |
| A55 | $O(CH_2CH_2O)_3CH_3$ | $O(CH_2)_nCON$-linker-oligo n = 1,2,3 | H | $CH_3$ or $CH_2CH_3$ | $CH_2(CH_2)_2OH$ | $CH_2(CH_2)_2OH$ |
| A56 | $O(CH_2CH_2O)_3CH_3$ | $O(CH_2CH_2O)_3CH_3$ | H | $CH_3$ or $CH_2CH_3$ | $CH_2(CH_2)_2OH$ | $CH_2(CH_2)_2OH$ |

TABLE C

Representative Substituents for Texaphyrin Macrocycles of the Present Invention ($R_5$, $R_6$, $R_9$, and $R_{10}$–$R_{12}$ are H)

| TXP | $R_1$ | $R_2$ | $R_3$ | $R_4$ | $R_7$ | $R_8$ |
|---|---|---|---|---|---|---|
| B1 | $CH_2(CH_2)_2OH$ | $CH_2CH_3$ | $CH_2CH_3$ | $CH_3$ | $O(CH_2)_3OH$ | $O(CH_2)_3OH$ |
| B2 | $CH_2(CH_2)_2OH$ | $CH_2CH_3$ | $CH_2CH_3$ | $CH_3$ | $O(CH_2CH_2O)_3CH_3$ | $O(CH_2CH_2O)_3CH_3$ |
| B3 | $CH_2(CH_2)_2OH$ | $CH_2CH_3$ | $CH_2CH_3$ | $CH_3$ | $O(CH_2)_nCON$-linker-site-directing molecule, n = 1–7 | $O(CH_2CH_2O)_3CH_3$ |
| B4 | $CH_2(CH_2)_2OH$ | $CH_2CH_3$ | $CH_2CH_3$ | $CH_3$ | $O(CH_2)_nCON$-linker-site-directing molecule | H |
| B5 | $CH_2(CH_2)_2OH$ | $CH_2CH_3$ | $CH_2CH_3$ | $CH_3$ | $OCH_2CO$-hormone | H |
| B6 | $CH_2(CH_2)_2OH$ | $CH_2CH_3$ | $CH_2CH_3$ | $CH_3$ | $O(CH_2CH_2O)_3CH_3$ | H |
| B7 | $CH_2(CH_2)_2OH$ | $CH_2CH_3$ | $CH_2CH_3$ | $CH_3$ | $OCH_2CON$-linker- | $O(CH_2CH_2O)_3CH_3$ |

TABLE C-continued

Representative Substituents for Texaphyrin Macrocycles of the
Present Invention ($R_5$, $R_6$, $R_9$, and $R_{10}$–$R_{12}$ are H)

| TXP | $R_1$ | $R_2$ | $R_3$ | $R_4$ | $R_7$ | $R_8$ |
|---|---|---|---|---|---|---|
| B8 | $CH_2(CH_2)_2OH$ | $CH_2CH_3$ | $CH_2CH_3$ | $CH_3$ | $OCH_2CO$-hormone site-directing molecule | $O(CH_2CH_2O)_3CH_3$ |
| B9 | $CH_2(CH_2)_2OH$ | $CH_2CH_3$ | $CH_2CH_3$ | $CH_3$ | $O(CH_2CH_2O)_{120}CH_3$ | $O(CH_2CH_2O)_3CH_2$—$CH_2$—N-imidazole |
| B10 | $CH_2(CH_2)_2OH$ | $CH_2CH_3$ | $CH_2CH_3$ | $CH_3$ | saccharide | H |
| B11 | $CH_2(CH_2)_2OH$ | $CH_2CH_3$ | $CH_2CH_3$ | $CH_3$ | $OCH_2CON(CH_2CH_2OH)_2$ | H |
| B12 | $CH_2(CH_2)_2OH$ | $CH_2CH_3$ | $CH_2CH_3$ | $CH_3$ | $CH_2CON(CH_3)CH_2$—$(CHOH)_4CH_2OH$ | H |
| B13 | $CH_2(CH_2)_2OH$ | COOH | COOH | $CH_3$ | $CH_2CON(CH_3)CH_2$—$(CHOH)_4CH_2OH$ | H |
| B14 | $CH_2(CH_2)_2OH$ | $COOCH_2CH_3$ | $COOCH_2CH_3$ | $CH_3$ | $CH_2CON(CH_3)CH_2$—$(CHOH)_4CH_2OH$ | H |
| B15 | $CH_2CH_2CON$—$(CH_2CH_2OH)_2$ | $CH_2CH_3$ | $CH_2CH_3$ | $CH_3$ | $CH_2CON(CH_3)CH_2$—$(CHOH)_4CH_2OH$ | H |
| B16 | $CH_2CH_2ON(CH_3)$—$CH_2(CHOH)_4CH_2OH$ | $CH_2CH_3$ | $CH_2CH_3$ | $CH_3$ | $OCH_3$ | $OCH_3$ |
| B17 | $CH_2(CH_2)_2OH$ | $CH_2CH_3$ | $CH_2CH_3$ | $CH_3$ | $O(CH_2)_nCOOH$, n = 1–7 | H |
| B18 | $CH_2(CH_2)_2OH$ | $CH_2CH_3$ | $CH_2CH_3$ | $CH_3$ | $(CH_2)_n$—CON-linker-site-directing molecule, n = 1–7 | H |
| B19 | $CH_2(CH_2)_2OH$ | $CH_2CH_3$ | $CH_2CH_3$ | $CH_3$ | $YCOCH_2$-linker site-directing molecule Y = NH, O | H |
| B20 | $CH_2CH_3$ | $CH_3$ | $CH_2CH_2$—COOH | $CH_3$ | $O(CH_2)_2CH_2OH$ | $O(CH_2)_2CH_2OH$ |
| B21 | $CH_2CH_3$ | $CH_3$ | $CH_2CH_2$—CON-oligo | $CH_3$ | $O(CH_2)_2CH_2OH$ | $O(CH_2)_2CH_2OH$ |
| B22 | $CH_2(CH_2)_2OH$ | $CH_2CH_3$ | $CH_2CH_3$ | $CH_3$ | $O(CH_2)_3CO$-histamine | H |

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cleavage of Plasmid DNA Using a
Texaphyrin-Lu(III) Complex

The present example demonstrates the use of a texaphyrin diamagnetic complex for the cleavage of DNA, in particular, the use of a Lu(III)txp complex for the cleavage of plasmid DNA, pGEM3Z and pBR322.

The bacterial strain used to harbor the plasmid DNA, pGEM3Z, was E. coli DH5α from Bethesda Research Laboratories (Gaithersburg, Md.). The plasmid used was pGEM3Z from Promega (Madison, Wisc.) with the 4.3 kb fragment of mouse MDR1a inserted at the EcoRI site. Growth conditions were LB (Luria broth) with ampicillin at 100 μg/mL. Cultures were inoculated and gently shaken overnight at 37° C.

A mini-prep of plasmid pGEM3Z DNA was obtained as follows. The pellet from 1.5 mL of an overnight culture was resuspended in 110 μL of solution A (25 mM Tris pH 8.9, 25 mM EDTA, 20% glucose and 1 mg/mL lysozyme). This suspension was left 5 min at room temperature, then 220 μL of solution B (0.2N NaOH, 1% SDS) was gently added. The tubes were mixed well and left to stand 5 min at room temperature. Then, 180 μL of 3M Na/K Acetate pH 5.2 (30 mL of 5M potassium acetate (KAc) and 20 mL of glacial acetic acid) was added, the tubes were mixed well, and spun 10 min. The cleared supernatant was transferred to fresh tubes and extracted with chloroform/isoamyl alcohol (24:1). The extracted aqueous layer was then precipitated with 1.0 mL of ethanol (200 proof) at room temperature. Tubes were mixed well and spun 10 minutes at room temperature. Pellets were dried briefly and resuspended in 100 μL of 1 X TE.

A large scale preparation of plasmid PGEM32 DNA was obtained as follows. The pellet from 1 L of an overnight culture was resuspended in 25 mL of solution A, lysed with 50 mL of solution B, and precipitated with 40 mL of 3M Na/KAc. The cleared lysate was filtered through sterile gauze and extracted with 100 mL of chloroform. The cleared, extracted lysate was then precipitated at room temperature with 70 mL of isopropyl alcohol. The pellet was then resuspended in 2 mL of 1 X TE. 2 gm of CsCl was added and dissolved. The solution was loaded into ultracentrifuge tubes with 0.5 mL of 10% sarcosyl and 0.5 mL of ethidium bromide (15 mg/mL). A solution of CsCl in 1 X TE (1 gm/mL) was added as an overlay until the tube was full. Tubes were spun until equilibrium was reached. Bands were pulled with a needle and syringe and were rebanded with more fresh overlay solution in the same or smaller size tubes and spun again. The respun band was pulled again with a needle and syringe, extracted 6X with butanol, dialyzed against several changes of 1 X TE, and ethanol precipitated. The pellet was resuspended in 1 X TE and the concentration determined by UV spectroscopy.

Lutetium(III) B2T2 texaphyrin ("LuB2T2 txp"; cpd. $1_A$, M=Lu) was prepared and described in WO 94/29316, the disclosure of which is incorporated herein by reference.

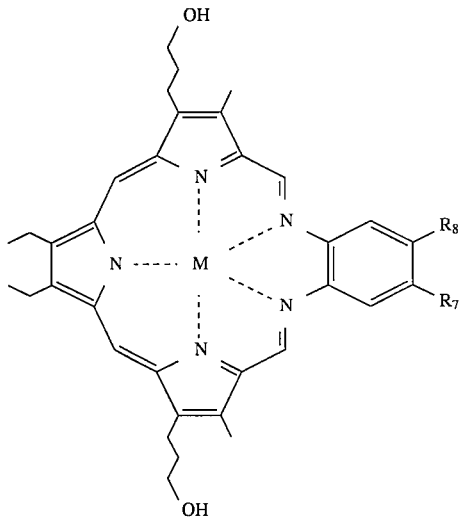

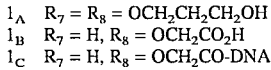

$1_A$  $R_7 = R_8 = OCH_2CH_2CH_2OH$
$1_B$  $R_7 = H, R_8 = OCH_2CO_2H$
$1_C$  $R_7 = H, R_8 = OCH_2CO$-DNA

Approximately 800 ng of plasmid DNA (10 μL, 10 mM Tris, 1mM EDTA) were mixed with stock solutions of LuB2T2 txp in DMSO to a final volume of 20 μL. Concentrations of 50, 100, and 200 μM LuB2T2 txp were tested. A control containing DMSO only was also included. The tubes containing the mixtures were allowed to incubate for 3 hours at 37° C. All samples were in duplicate: one tube was left in a bacterial incubator wrapped in foil (the "dark" sample) and the second tube was kept in a tissue culture incubator with fluorescent lights on (the "light" sample). After 3 hours, the samples were loaded onto 0.8% agarose gels in 1× TAE and electrophoresis was carried out with ethidium bromide present. HindIII digested λ DNA was included as molecular weight markers.

DNA bands were present in the control lane and in the lane for the 50 μM LuB2T2 txp sample held in the dark. The sample exposed to light at 50 μM LuB2T2 was degraded. In all the other samples with greater concentrations of texaphyrin, the DNA was precipitated by the LuB2T2 txp.

Further samples of supercoiled plasmid pGEM3Z were purified by cesium chloride density gradient centrifugation, after which ~200 ng was mixed with various concentrations of LuB2T2 txp in distilled water to a final volume of 20 μL. Concentrations of 1, 5, 10, 25 and 50 μM of LuB2T2 txp were tested. Following the procedures described above, light and dark samples were incubated for 2 hours and then were applied to a 0.8% 1× TAE agarose gel and electrophoresis was carried out in the presence of ethidium bromide. A control without LuTxp was also run. Hind III digested λ DNA was included as a molecular weight marker.

At 25μM texaphyrin incubated in the light, less material was present in the lower band (supercoiled DNA) and it had shifted up to the higher band (nicked circle), indicating some DNA strand cleavage. There was no difference for the 25 μM txp sample held in the dark or at lower concentrations of LuTxp compared to the control. Therefore, DNA is not degraded at these lower concentrations under these conditions. At 50 μM LuB2T2 txp, the DNA was precipitated.

To determine the degradation potential of texaphyrins for linearized DNA, 250 ng of linearized DNA (obtained by digestion of pGEM3Z plasmid and gel isolation) was mixed with either LuB2T2 txp or with lutetium acetate in distilled water to a final volume of 20 μL. The samples were: 50μM LuB2T2 txp; 50μM LuB2T2 txp+25 mM EDTA; 50 μM LuB2T2 txp+free phosphate at 100, 10, or 1 μM; 25 μM LuB2T2 txp; 25 μM LuB2T2 txp+25 mM EDTA; 50 μM Lu acetate; 50 μM Lu acetate+25 mM EDTA; 50 μM Lu acetate+free phosphate at 100, 10 or 1 μM; and 100 μM phosphate only, as the control. Following the procedures described above, light and dark samples were incubated for 2 hours and then individually separated by electrophoresis on a 0.8% 1× TAE agarose gel with ethidium bromide.

LuB2T2 txp precipitated the linearized DNA at 50 μM with or without EDTA or free phosphate. At 25 μM LuB2T2 txp, both with and without EDTA, there was a difference between the light and dark samples; the light reaction resulted in DNA degradation while the dark reaction left the material intact. The presence of free phosphate had no effect on the degradation of DNA. Free lutetium, either alone or in the presence of phosphate, did not degrade DNA. The band containing free lutetium with EDTA showed a barely detectable loss of intensity and also smearing, so that there may have been some precipitation of DNA, possibly due to the high concentration of EDTA.

In another experiment, 350 ng of linearized pGEM3Z DNA were mixed with 1, 5, 10, 25, or 50 μM of LuB2T2 txp, and samples were separated by electrophoresis on agarose gels as described above. At 50 μM LuB2T2 txp, the DNA was precipitated by the LuB2T2 txp. At 25 μM of the texaphyrin in the light sample, there was a less intense signal, indicating degradation of the DNA. The DNA was not degraded for the 25 μM txp dark reaction or the lower concentrations of the texaphyrin.

In a further experiment, pBR322 plasmid DNA was found to be cleaved by LuB2T2 Txp at a concentration of 4 μM. The experimental conditions were as follows: Irradiated solutions contained 100 μL 0.1 SSC buffer (saline sodium citrate: 15 mM NaCl, 1.5 mM sodium citrate, pH 7.0), 32 μM pBR322 DNA phosphates and either 0 or 4 μM LuTxp. Plasmid pBR322 was purchased from Gibco BRL and contained greater than 90% supercoiled DNA. Solutions were irradiated at room temperature with a high pressure Xenon lamp through a pyrex filter to stop UV light of wavelengths below about 300 nM. Samples were irradiated in a quartz cuvette measuring 1 mm in diameter and received approximately 3400 W/m$^2$. After irradiation, 3 μL 50% glycerol/water loading buffer containing bromophenol blue was added to 9 μL irradiated solution. The samples were analyzed on a 0.8% agarose gel containing ethidium bromide in tris-acetate buffer at 90 V for 30 minutes. The DNA was detected by fluorescence using a UV lamp.

No nicking or cleavage was seen in a control sample without texaphyrin or in a control sample with texaphyrin but without light. In the presence of LuB2T2 Txp and light for 5, 10, and 20 minutes, the supercoiled form of the DNA gradually disappeared and the relaxed form appeared. A small amount of linear DNA was also formed.

It has been observed by the present inventors that light plays an important role in the cleavage mechanism since cleavage occurs in the light but not in the dark. Diamagnetic metal cations such as In(III), Y(III), La(III), Zn(II), or Cd(II) may also effect cleavage since texaphyrin complexes of these metal cations are photosensitive.

EXAMPLE 2

A Texaphyrin-Paramagnetic Metal Complex Does Not Effect DNA Cleavage

The present example demonstrates the activity of a diamagnetic metal Lu(III)texaphyrin complex for light-activated cleavage of DNA, and compares it with the lack of cleavage activity by a paramagnetic metal Dy(III)texaphyrin complex.

Ten µL (approximately 200,000 cpm) of 5'-$^{32}$P-labelled DNA 36-mer ($8_B$ of FIG. 8) was added to a solution of 10 µL of 4× buffer (400 mM NaCl, 200 mM HEPES, pH 7.5, 100 µM EDTA). To this was added 20 µL of either 2 µM lutetium(III) B2T2 texaphyrin (LuB2T2 txp; cpd. $1_A$, M=Lu) or 2 µM dysprosium(III) B2T2 texaphyrin (DyB2T2 txp; cpd. 1A, M=Dy) in deionized water to give a final volume of 40 µL reaction solution in an Eppendorf tube. Final texaphyrin complex concentration was 1 µM. Two tubes of reaction mixture containing LuB2T2 txp and two tubes of reaction mixture containing DyB2T2 txp were prepared. An additional reaction mixture was prepared in the same way, except that an equal volume of water was substituted for the texaphyrin solution, as the control. One of each of the LuB2T2 txp and DyB2T2 txp tubes was left in a bacterial incubator wrapped in foil (the "dark" sample) and the second tube containing each complex was kept in a tissue culture incubator with fluorescent lights on (the "light" sample). The control tube was kept in the light and was not incubated. The texaphyrin tubes were incubated overnight (ca. 14 hours) at 37° C., after which all samples were loaded onto a polyacrylamide gel and separated by electrophoresis following procedures described herein.

In the control sample, a DNA band was present corresponding to the 36-mer substrate. In the DyB2T2 txp lanes, both light and dark, and in the LuB2T2 txp dark lane, a DNA band of the same size was present. However, the DNA was degraded in the LuB2T2 txp sample exposed to light indicating that, in the presence of light, the diamagnetic texaphyrin complex cleaved the DNA.

EXAMPLE 3

Comparison of Cleavage by a Texaphyrin, a Sapphyrin and a Porphyrin

LuT2B2 txp (cpd. $1_A$) and a sapphyrin (cpd. 3) were screened for their photocleavage capabilities against the known photocleaving agent meso-tetrakis(4-N-methylpyridyl)porphine (TMPyPH$_2$; purchased from Aldrich Chemical Co.), using a general pBR322 plasmid DNA assay.

Following the general procedure of Praseuth, D. et al. (Photochem. Photobiol., 44 (1986), 717–724) and Croke, D. et al. (J. Photochem. Photobiol., B 18 (1993), 41–50, pBR322 plasmid DNA (20.4 ng/µL) was irradiated in quartz cuvettes in the presence of either LuB2T2 txp, the sapphyrin or TMPyPH$_2$. Irradiation was effected at room temperature for 60 min. using light from a high-pressure xenon lamp (Oriel). In the first group of tests, white light was used. In the second group, the light was passed through a 700 nm filter (CVI Laser). Each sample received approximately 280 mW/cm$^2$. Additional cuvettes containing the DNA and each chromophore were not exposed to the light. DNA cleavage was followed by monitoring of the conversion of supercoiled (form I) plasmid DNA to the nicked circular (form II) DNA.

At wavelengths above 300 nm, all three compounds showed efficient photocleavage. When, however, the shorter wavelengths were blocked out with a 700 nm filter, cleavage efficiences of 8%, 17% and 93% were recorded for the phorphyrin control, the sapphyrin and LuB2T2 txp, respectively.

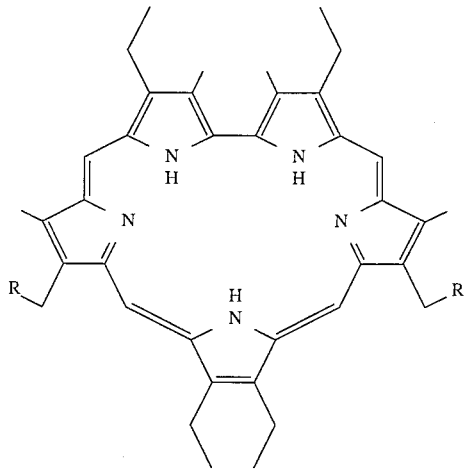

3  R = CH$_2$CON(CH$_2$CH$_2$OH)$_2$

EXAMPLE 4

Synthesis of a T2B1 TXP metal complex-oligonucleotide conjugate

Figure 1B:
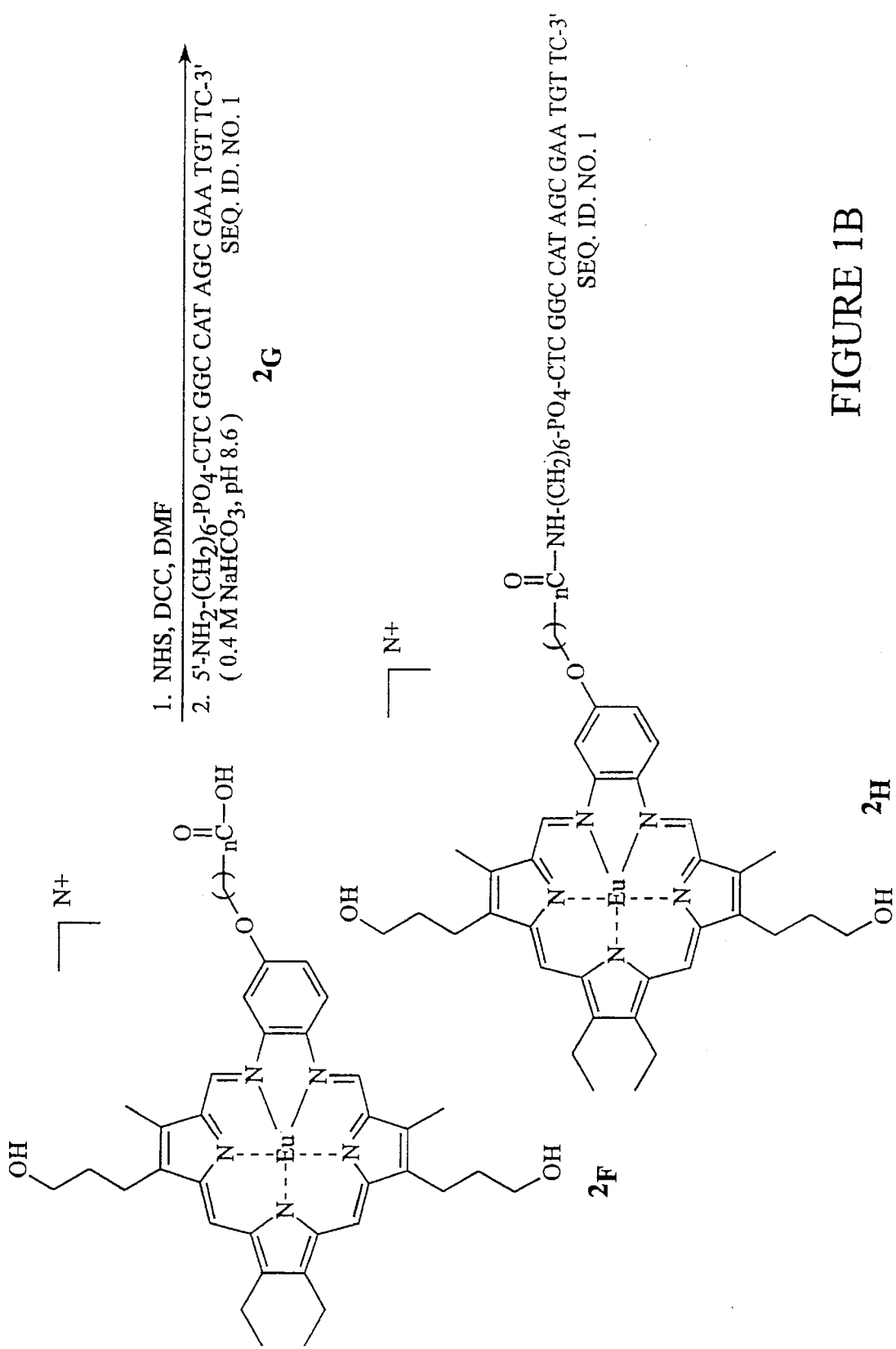

The present example provides for the synthesis of a texaphyrin metal complex-oligonucleotide conjugate useful for site-directing cleavage of a complementary DNA (see FIG. 1A and FIG. 1B).

4-Amino-1-[1-(ethyloxy)acetyl-2-oxy]-3-nitrobenzene $2_B$, n=1. Potassium carbonate (14.0 g, 101 mmol) and 4-amino-3-nitrophenol $2_A$ (10.0 g, 64.9 mmol) were suspended in 150 mL dry acetonitrile. Ethyl-2-iodoacetate (10 mL, 84.5 mmol) (or ethyl iodobutyrate may be used, in that case n=3) was added via syringe, and the suspension was stirred at ambient temperature for ca. 21 h. Chloroform (ca. 375 mL) was added and was used to transfer the suspension to a separatory funnel, whereupon it was washed with water (2× ca. 100 mL). The water washes were in turn washed with CHCl$_3$ (ca. 100 mL) and the combined CHCl$_3$ extracts were washed with water (ca. 100 mL). Solvents were removed on a rotary evaporator, and the residue was redissolved in CHCl$_3$ (ca. 500 mL) and precipitated into hexanes (1.5 L). After standing two days, the precipitate was filtered using a coarse fritted funnel and dried in vacuo to provide 14.67 g compound $2_B$, n=1 (94.1%). TLC: Rf=0.43, CHCl$_3$.

4-Amino-1-[1-(hydroxy)acetyl-2-oxy]-3-nitrobenzene $2_c$, n=1. 4-Amino-1-[1-(ethyloxy)acetyl-2-oxy]-3-nitrobenzene $2_B$, n=1, (10.00 g, 37.3 mmol) was dissolved in tetrahydrofuran (100 mL), aqueous sodium hydroxide (1M solution, 50 mL) was added and the solution was stirred at ambient temperature for ca. 21 h. Tetrahydrofuran was removed on a rotary evaporator, and water (100 mL) was added. The solution was washed with CHCl$_3$ (ca. 200 mL), then neutralized by addition of hydrochloric acid (1M solution, 50 mL). The precipitate which formed was filtered after standing a few minutes, washed with water, and dried in vacuo to provide 8.913 g compound $2_C$, n=1 (99.5%). TLC: Rf=0.65, 10% methanol/CHCl$_3$.

16-[1-(Hydroxy)acetyl-2-oxy]-9,24-bis(3-hydroxypropyl)-4,5-diethyl-10,23-dimethyl-13,20,25,26,27-pentaazapentacyclo-[20.2.1.1$^{3,6}$.1$^{8,11}$0$^{14,19}$]heptacosa-3,5,8,10,12, 14(19), 15,17,20,22,24-undecaene $2_E$, n=1. 4-Amino-1-[1-(hydroxy)acetyl-2-oxy]-3-nitrobenzene $2_C$, n=1 (1.800 g, 8.49 mmol) was dissolved in methanol (100 mL) in a 1 L flask. Palladium on carbon (10%, 180 mg) was added, and the atmosphere inside the flask was replaced with hydrogen at ambient pressure. A grey precipitate was formed after ca. 3 h, and the supernatant was clear. Methanol was removed in vacuo, taking precautions to prevent exposure to oxygen, and the compound was dried overnight in vacuo. Isopropyl alcohol (500 mL) and HCl (12M, 400 μL) were added, and the suspension was allowed to stir for ca. 15'. 2,5-Bis[(3-hydroxypropyl-5-formyl-4-methylpyrrol-2-yl)methyl]-3,4-diethylpyrrole $2_D$ (n=1) (4.084 g, 8.49 mmol) was added, and the reaction stirred at room temperature under argon for 3 hours. Hydrochloric acid was again added (12M, 400 μL) and the reaction again was allowed to stir for an additional 3.5 h. The resulting red solution was filtered through celite, and the filtercake was washed with isopropyl alcohol until the filtrate was colorless. Solvent was reduced to a volume of ca. 50 mL using a rotary evaporator, whereupon the solution was precipitated into rapidly stirring Et$_2$O (ca. 700 mL). Compound $2_E$ (n=1) was obtained as a red solid (5.550 g, 98.4%) upon filtering and drying in vacuo. TLC: R$_f$=0.69, 20% methanol/CHCl$_3$ (streaks, turns green on plate with I$_2$).

Metal complex of 16-[1-(hydroxy)acetyl-2-oxy]-9,24-bis(3-hydroxypropyl)-4,5-diethyl-10,23-dimethyl-13,20,25, 26,27pentaazapentacyclo[20.2.1.1$^{3,6}$.1$^{8,11}$.0$^{14,19}$]heptacosa-1,3,5,7,9,11(27),12,14(19),15,17,20,22(25),23-tridecaene $2_F$, n=1. Approximately equal molar amounts of the protonated form of the macrocycle, 16-[1-(hydroxy)acetyl-2-oxy] -9,24-bis(3-hydroxypropyl)-4,5-diethyl-10,23-dimethyl-13, 20,25,26,27-pentaazapentacyclo-[20.2.1.1$^{3,6}$.1$^{8,11}$0$^{14,19}$] heptacosa-3,5,8,10,12,14(19),15,17,20,22,24-undecaene hydrochloride $2_E$, n=1, and a metal acetate pentahydrate were combined with triethylamine in methanol, and were heated to reflux under air for 5.5 h. The reaction was cooled to room temperature, and stored at −20° C. overnight. Solvent was removed on a rotary evaporator, acetone was added, and the suspension was stirred on a rotary evaporator for 2 h. The suspension was filtered and the precipitate dried briefly in vacuo, whereupon a solution was formed in methanol (ca. 250 mL) and water (25 mL). The pH was adjusted to 4.0 using HCl (1M), HCl.washed zeolite LZY54 was added (ca. 5 g) and the suspension was stirred on the rotary evaporator for ca. 6 h. Amberlite™ IRA-900 ion exchange resin (NaF treated, ca. 5 g) was added, and the suspension was stirred for an additional hour. The suspension was filtered, the resin was washed with methanol (ca. 100 mL), and the filtrate was adjusted to pH 4.0 using HCl (1M). Solvents were removed on a rotary evaporator, using ethanol (abs.) to remove traces of water. After drying in vacuo, the compound was dissolved in methanol (25 mL) and precipitated into rapidly stirring Et$_2$O (300 mL). Compound $2_F$, n=1, was obtained as a precipitate after filtering and drying in vacuo. An analytical sample was prepared by treating 50 mg of $2_F$, n=1, dissolved in methanol (25 mL) with acetic acid-washed zeolite, then acetic acid-washed Amberlite™ for ca. 1 h. After reducing methanol to a minimum volume, the solution was precipitated into rapidly stirring Et$_2$) (70 mL), filtered, and dried in vacuo.

Postsynthetic modification of oligodeoxynucleotideamine $2_G$ with metal complex $2_F$, n=1. The metal complex of 16-[1-(hydroxy)acetyl-2-oxy]-9,24-bis(3-hydroxypropyl)-4,5-diethyl-10,23-dimethyl-13,20,25,26,27-pentaazapentacyclo[20.2.1.1$^{3,6}$.1$^{8,11}$.0$^{14,19}$]heptacosa-1,3,5,7,9,11 (27),12,14(19),15,17,20,22(25),23-tridecaene $2_F$, n=1, (about 30 μMol) and N-hydroxysuccinimide (43 μMol) were dried together overnight in vacuo. The compounds were dissolved in dimethylformamide (anhydrous, 500 μL) and dicyclohexylcarbodiimide (10 mg, 48 μMol) was added. The resulting solution was stirred under argon with protection from light for 8h, whereupon a 110 μL aliquot was added to a solution of oligodeoxynucleotide $2_G$ (87 nmol) in a volume of 350 μL of 0.4M sodium bicarbonate buffer in a 1.6 mL Eppendorf tube. After vortexing briefly, the solution was allowed to stand for 23 h with light protection. The suspension was filtered through 0.45 μM nylon microfilterfuge tubes, and the Eppendorf tube was washed with 150 μL sterile water. The combined filtrates were divided into two Eppendorf tubes, and glycogen (20 mg/mL, 2 μL) and sodium acetate (3M, pH 5.4, 30 μL) were added to each tube. After vortexing, ethanol (absolute, 1 mL) was added to each tube to precipitate the DNA. Ethanol was decanted following centrifugation, and the DNA was washed with an additional 1 mL aliquot of ethanol and allowed to air dry. The pellet was dissolved in 50% formamide gel loading buffer (20 μL), denatured at 90° C. for ca. 2', and loaded on a 20% denaturing polyacrylamide gel, and electrophoresed with protection from light. The band corresponding to conjugate $2_H$, n=1, was cut from the gel, crushed, and soaked in 1× TBE buffer (ca. 7 mL) for 1–2 days. The suspension was filtered through nylon filters (0.45 μM) and desalted using a Sep-pak™ reverse phase cartridge. The conjugate was eluted from the cartridge using 40% acetonitrile, lyophilized overnight, and dissolved in 1mM HEPES buffer, pH 7.0 (500 μL). The solution concentration was determined using UV/vis spectroscopy.

EXAMPLE 5

Synthesis of Texaphyrin-Oligonucleotide Conjugates Having a Texahyrin Attached to the 3' end Two oligodeoxyribonucleotides of 12 bases each were synthesized to contain alkylamine groups at the 3' terminal phosphate (Keystone Labs, Menlo Park, Calif.). Oligonucleotides were HPLC purified and precipitated using LiCl prior to use. Reaction of a carboxylic acid functionalized metal texaphyrin complex such as $1_B$, with carbodiimide and N-hydroxysuccinimide produced the corresponding activated ester, which was added directly to a solution of the chosen oligodeoxynucleotide amine. The resulting txp-metal complex-oligonucleotide conjugates were purified by electrophoresis.

These 3'-conjugates may be of particular importance in certain embodiments of the present invention, since attachment of large groups (such as the present texaphyrin complexes) to the 3' end of oligonucleotides renders the oligonucleotide resistant to cellular exonucleases.

In a similar manner, an embodiment of the present invention is the addition of particular ligands to the 3' end of an oligonucleotide having its 5' end conjugated to a texaphyrin. The function of the 3' ligand is to aid in the uptake of the conjugate into the cell. Such ligands are known in the art and include, but are not limited to, cholesterol and polylysine.

A further embodiment of the present invention in the cleavage of DNA using texaphyrin metal complex-oligonucleotide conjugates is the use of a set of two conjugates, one having the texaphyrin metal complex conjugated to the 5' end of an oligomer and the other having a texaphyrin metal complex conjugated to the 3' end of an oligomer and the oligomers are complementary to the same DNA substrate, one just upstream from the other, so as to position both texaphyrin metal complexes in proximity to the targeted cleavage site. The distance separating the two catalytic groups may be varied by preparing a nested set of oligomer-5'-conjugates of varying lengths and comparing the cleavage efficiencies that result upon the simultaneous binding of the two conjugates to the DNA template.

EXAMPLE 6

Synthesis of a Texaphyrin Metal Complex-Oligonucleotide Dual Conjugate

An oligodeoxyribonucleotide having 12 bases was synthesized to contain alkylamine groups at both the 3' and the 5' ends (Keystone Labs, Menlo Park, Calif.). This oligomer was reacted with an excess of a carboxylic acid functionalized metal-texaphyrin complex $1_B$, following the procedures of Example 4, to give a dual conjugate having a texaphyrin-metal complex at both the 3'- and the 5'-ends of the 12-mer.

The use of two texaphyrin-metal complexes conjugated to the same oligonucleotide, one at each end, should effect the cleavage of DNA with increased efficiency due to the concerted activity of the metal complexes. In this embodiment, it is preferred that both of the texaphyrin complexes contain the same metal, preferably a diamagnetic metal cation and more preferably lutetium(III).

Further, a dual conjugate provides versatility in the functions that may be accomplished by this one molecule. For example, the oligonucleotide provides binding specificity, one texaphyrin metal complex may provide for imaging (having Gd(III) as the metal ion, for example) while the other provides for DNA cleavage. Such a dual conjugate allows for two functions, imaging and cleavage, to be effected by one molecule.

EXAMPLE 7

Site-Specific Light-Dependent Cleavage of DNA by LuTxp-Oligonucleotide Conjugate The present example provides for the site-specific light-dependent cleavage of DNA by Lutetium(III) texaphyrin-oligonucleotide conjugate.

Figure 2:
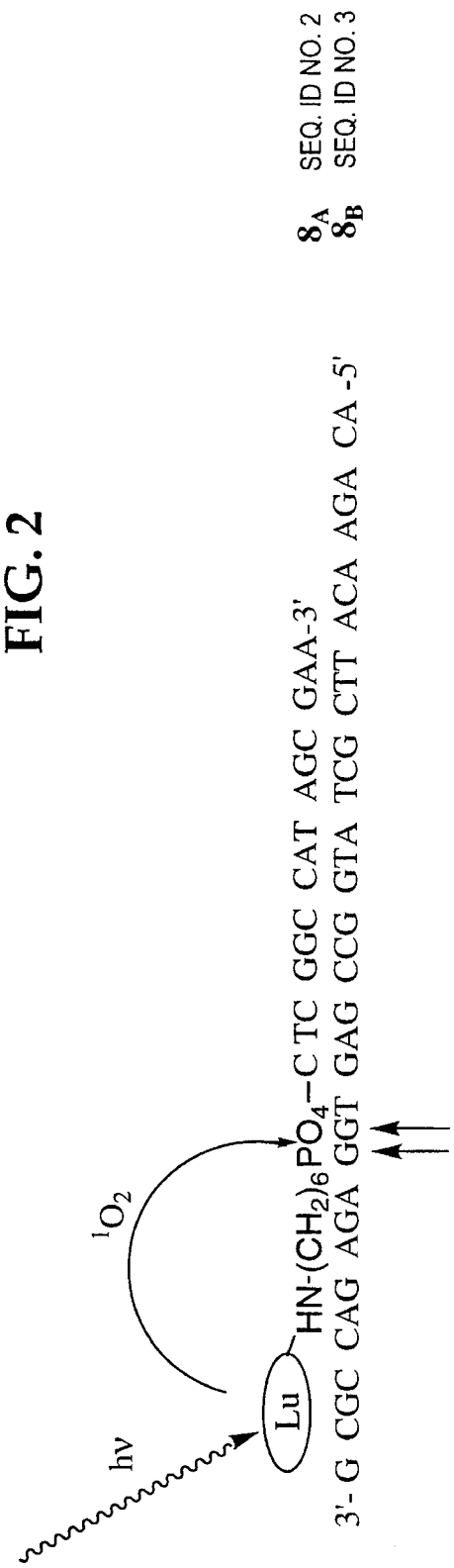
FIG. 2 shows site-specific cleavage of DNA by a Lu(III)Txp-oligodeoxynucleotide conjugate.

A reaction mixture was prepared by adding ca. 300,000 cpm of 5'-$^{32}$P-labeled DNA 36-mer ($8_B$ of FIG. 2) (4µL) to a solution made from lutetium(III) texaphyrin conjugate ($8_A$ of FIG. 2; prepared as described in publn. WO 94/29316) (2.5 µL, 407 nM stock solution), 4× buffer (5 µL) and water (8.5 µL) to produce a final volume of 20 µL. Final conjugate concentration was 50 nM. The 4× buffer is 400 mM NaCl, 200 mM HEPES, pH 7.5, 100 µM EDTA. Eight reaction mixtures were pipetted into O-ring type Eppendorf tubes (1.6 mL). Two additional reaction mixtures (tubes 1 and 6) were prepared in the same way, except that an equal volume of water was substituted for the LuTx-DNA conjugate. Tubes 1–5 were covered with an atmosphere of oxygen, and tubes 6–10 with an atmosphere of argon. Samples were sealed with parafilm, vortexed and centrifuged briefly, and then irradiated with laser light via the side of the Eppendorf tube. The laser was set at 752 nm and a power density of ca. 150 mW/cm$^2$ was used (ca. 20% reduction of laser power density is estimated to occur due to attenuation by the Eppendorf tube). Samples were irradiated for 1, 5, 10, or 30 minutes, whereupon the DNA was precipitated with ethanol using standard methods. The samples were resuspended in 50% formamide loading buffer, denatured at 90° C. for 5 minutes, and analyzed by electrophoresis on a 20% denaturing polyacrylamide gel.

Control reactions containing free LuB2T2 Txp were prepared by adding ca. 300,000 cpm of 5'-$^{32}$P-labeled DNA 36-mer $8_B$ (4 µL) to a solution made from LuB2T2 Txp (cpd. $1_A$, M=Lu) (5 µL, 2 µM stock solution), 4× buffer (5 µL) and water (6 µL) to produce a final volume of 20 µL. Final LuB2T2 Txp complex concentration was 500 nM. Eight reaction mixtures were pipetted into O-ring type Eppendorf tubes (1.6 mL). Two additional reaction mixtures (tubes 11 and 16) were prepared in the same way, except that an equal volume of water was substituted for the LuB2T2 pTx solution. Tubes 11–15 were covered with an atmosphere of oxygen, and tubes 16–20 with an atmosphere of argon. Samples were irradiated, ethanol precipitated, and analyzed by electrophoresis as described above.

The autoradiograph indicated substantial cleavage only in those lanes (2–5, 7–10) which contained the 12-mer LuTx-DNA conjugate $8_A$. The cleavage sites covered four residues, proximal to the anticipated location of the LuTx-DNA conjugate. Both the location of cleavages and the much greater efficiency of conjugate cleavage relative to that caused by free complex are consistent with a model whereby hybridization of the DNA increases the local concentration of the LuTx and effects site-specific cleavage.

The autoradiograph also contained information regarding cleavage mechanism: The presence of oxygen in reactions 2–5 clearly increased the efficiency of DNA strand breakage. That cleavage occurred at all in lanes 7–10 is presumably attributable either to ambient light prior to the layering with argon, or else to incomplete replacement of the atmosphere in these tubes. The positive effect of oxygen on cleavage implicates singlet oxygen or another oxygen product as the intermediary species responsible for DNA strand breakage.

The maximal extent for cleavage observed was roughly 5% and was obtained after 5 minutes of laser irradiation. It is possible that the actual yield of reaction is far greater, since the initial step in cleavage is likely a nicking step and complete cleavage would be facilitated, for example, in vitro, by an organic base such as piperidine. Not wanting to be bound by theory, it is possible that singlet oxygen attacks a purine base, guanine for example, and causes depurination of double-stranded DNA similar to the Maxam and Gilbert chemical cleavage of DNA.

Further irradiation had no effect on the amount of cleavage. This observation is consistent with self-destruction of the 12-mer LuTx conjugate (which is also composed of DNA) or may reflect an instability of the LuTx complex towards laser light. The disappearance of low mobility material assigned as non-denatured DNA-LuTx conjugate duplex at greater laser irradiation times provides additional support for these possibilities.

EXAMPLE 8

Sequence Specific Light-Dependent Cleavage of DNA by LuTxp Conjugated to 2'-O-Methyl RNA The present example provides for the site-specific light-dependent cleavage of DNA by lutetium(III) texaphyrin 2'-O-methyl RNA oligonucleotide conjugates.

Figure 3:
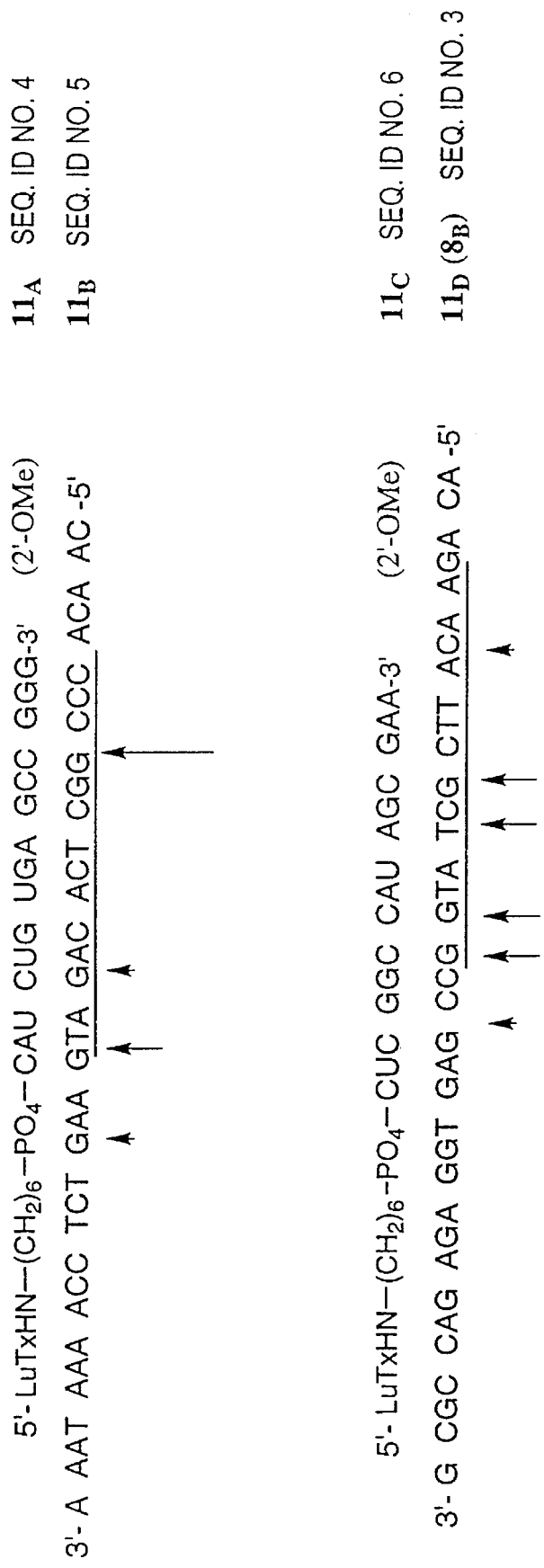
FIG. 3 shows lutetium texaphyrin-RNA analog oligonucleotide conjugates hybridized to template DNA. The RNA analog is the 2'-O-methylated derivative of the ribonucleotide.

Reaction mixtures were prepared by adding ca. 100,000 cpm of 5'-$^{32}$P-labeled DNA 36-mer $11_D$ or $11_B$ (FIG. 3) to solutions made from lutetium(III) texaphyrin conjugate $11_A$ (1.0 μL, 968 nM stock solution) or $11_C$ (3.0 μL, 335 nM stock solution), 4× buffer (5 μL) and water to produce a final volume of 20 μL. Final conjugate concentration was 50 nM. The 4× buffer is 400 mM NaCl, 200 mM HEPES, pH 7.5, 100 μM EDTA. Two conjugate-free controls (samples 1 and 8) were prepared by substituting water for conjugate solution. Samples 1, 4–8, and 11–14 were irradiated for 4.5 hours at 37° C. using a 75 watt incandescent light at ca. 9 inches above the heating block. Samples 2, 3, 9, and 10 were incubated without exposure to light at 37° C. The DNA was precipitated with ethanol using standard methods following incubation. Samples 6, 7, 13, and 14 were dissolved in 10% aqueous piperidine solution (50 μL), heated at 90° C. for 30 minutes, then freeze-dried. All samples were resuspended in 50% formamide loading buffer, denatured at 90° C. for 5' and analyzed by electrophoresis on a 20% denaturing polyacrylamide gel.

The autoradiograph indicated substantial cleavage only in those lanes (5, 7, 11, and 13) that contained the appropriate complementary 15-mer LuTx 2'-O-methyl RNA conjugate. The cleavage sites covered three to four residues, proximal to the anticipated location of the LuTx complex. These cleavages are consistent with a model whereby hybridization of the 2'-O-methyl-LuTx conjugates to their complementary sequences of DNA increases the local concentration of the LuTx and effects site-specific cleavage.

The autoradiograph also contained information regarding cleavage mechanism: Certain positions within the cleavage site are clearly more reactive to cleavage than others. Definitive identification of these more reactive bases awaits further experimentation, but are tentatively assigned to positions containing purine bases.

The maximal extent of cleavage observed was roughly 10%, and was obtained using a piperidine treatment of the light-exposed samples. The effect of this piperidine treatment is at least a 10-fold increase in cleavage products, indicating that initial DNA lesions formed by the photochemical reaction require base assistance to efficiently produce strand breaks. As the extent of light-induced cleavage in non-piperidine-treated lanes is far lower than that obtained using laser irradiation (cf., Example 7) it may be possible to observe an increase in the yield of cleavage products by using both laser and piperidine treatments.

This test was repeated under more optimized conditions (see, Magda, D. et al., *J. Am. Chem. Soc.*, 117 (1995), 3629–3630). The extent of photocleavage is now routinely 80% –90% using 732 nm light.

A txp-oligonucleotide conjugate of a derivatized RNA such as the 2'-O-methyl RNA analog used herein may provide stability against self-cleavage. RNA is hydrolyzed by LuTx; however, the 2'-O-Me RNA lacks a 2'-OH and, therefore, is stable to hydrolysis. Therefore, an RNA analog oligomer may be more stable than a DNA oligomer for the Txp-oligonucleotide conjugate. The synthesis of RNA analog-conjugates is the same as for Txp-DNA conjugates discussed previously herein. An RNA-analog conjugate may be complementary to an antisense or a sense strand of DNA and forms a triple helix in the process of binding to a double helix.

EXAMPLE 9

Photocleavage of a Double-Stranded DNA

This example illustrates the site-specific, light-dependent cleavage of double-stranded DNA by LuTx-DNA conjugates (cpd. $1_C$).

Figure 4:
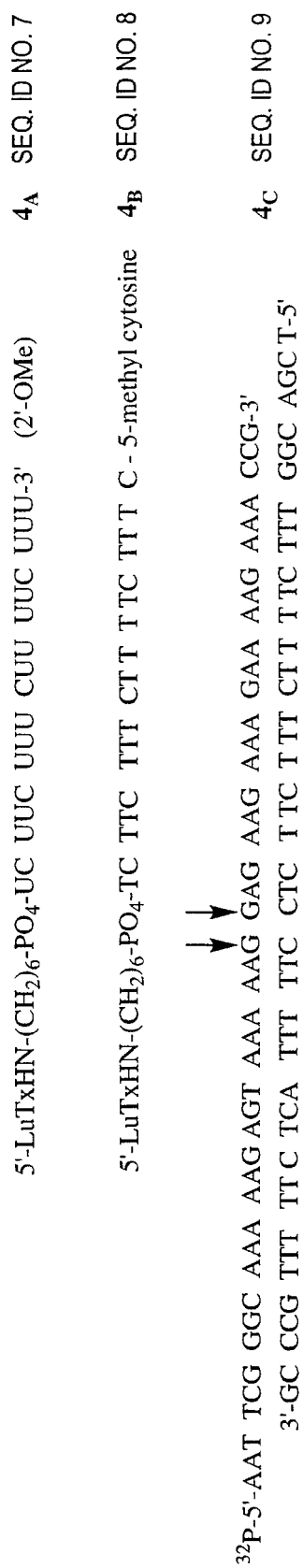
FIG. 4 shows site-specific cleavage of double-stranded DNA by lutetium texaphyrin-oligonucleotide conjugates.

Reaction mixtures were prepared by adding LuTx conjugate $4_A$ or $4_B$ (see FIG. 4) to solutions containing the double-stranded target DNA oligonucleotide $4_C$, which was labelled with $^{32}p$ as indicated. Ca. 30,000 cpm $^{32}p$ was used per reaction, with 4× buffer (5 μL; 400 mM NaCl, 200 mM HEPES, pH 6.0 or 6.8, 4 mM Sermine), carrier DNA (1 μL) and water to produce a final volume of 20 μL. Final conjugate concentrations were 1, 0.1 and 0.01 μM. All reactions were heated for 10 min. at 37° C. and allowed to cool slowly to ambient temperature, after which they were incubated for 1 hr. Care was taken to keep the samples protected from light.

The samples were then irradiated for 15 min. at ambient temperature using a dye laser (Coherent, Palo Alto, Calif.) tune to 732 nm and with a power density of 150 mW/cm². Following irradiation, the DNA was precipitated with ethanol using standard methods. Samples containing radiolabelled DNA were dissolved in 10% aqueous piperidine solution (100 μL) and heated at 90° C. for 30 min., then dried on a Speedvac. All samples were resuspended in 50% formamide loading buffer, denatured at 60° C. for 3 min., and analyzed by electrophoresis on a 20% denaturing polyacrylamide gel.

The autoradiograph indicated cleavage products in lanes where the concentration of LuTx-DNA conjugates were 1 μM. No cleavage products were seen at the lower concentrations tested except for those incubated with $4_A$ at pH 6.0. The LuTx-mediated DNA cleavage bands co-migrated with bands generated by dimethylsulfate in the guanine-specific sequencing lanes. The cleavage products produced by the LuTx conjugates are consistant with the triplex formation and the ability to bring the lutetium texaphyrin in close proximity to the guanine bases at positions 24 and 25 on the target strand, as indicated by the arrows in FIG. 4. The total efficiency of DNA photocleavage by the LuTx conjugates ranged from 2–3%.

The following references are incorporated in pertinent part by reference herein for the reasons cited below.

REFERENCES

Brown, S. B. and T. G. Truscott., *Chemistry in Britain*, 955–958, Nov. 1993.
Caracciolo et al. *Science*, 245:1107, 1989.
Chen, C. H. B. and Sigman, D. S., *J. Amer. Chem. Soc.*, 110:6570–6572, 1988.
Dervan, *Science*, 232:464–471, 1986.
Dreyer and Drevan, *Proc. Natl. Acad. Sci. USA*, 82:968–972, 1985.
Fiel, *Journal of Biomolecular Structure & Dynamics*, 6 (6): 1259–1275, 1989.
Goodchild, J. , *Bioconjugate Chemistry.*, 1:165–187, 1990.
Grossweiner, L. I., *Lasers, Surg. Med.*, 11:165–173, (1991).
Groves and Farrell, *J. Am. Chem. Soc.*, 111:4998–5000, 1989.
Henderson, B. W. and T. J. Dougherty, *Photochem., Photobiol.*, 55:145–157, 1992.
Kobayashi, et al., *Photomed. Photobiol.*, 15 (1993).
Le Doan et al., *Biochemistry*, 25:6736–6739, 1986.
Le Doan et al., *Bioconjugate Chem.*, 1:108 (1990).
Le Doan et al., *Nucleic Acids Research*, 15(21):8643–8659, 1987.
Lee et al., *Biochemistry*, 27:3197–3203, 1988.
Lin, et al. , *Biochemistry*, 28:1054–1061, 1989.
Meunier, B., et al., *Bioconjugate Chem.*, 4:366–371.
Moan, J. and K. Berg, *Photochem. Photobiol.*, 55:931–948, 1992.

PCT/US94/06284.
Praseuth et al., *Photochemistry and Photobiology*, 44:717–724, 1986.
Sessler et al., *Comm. Inorg. Chem.*, 7:333, 1988.
Sessler et al., *SPIE Proc. Soc. Opt. Eng.*, 1426:318–329, 1991.
Sindelar et al., *Arch. Surg.*, 126:318–324, 1991.
Skikes, J. D., *Photochem. Photobiol.*, 43:691, 1986.
Strobel and Dervan, *J. Am. Chem. Soc.*, 111(18):7826–7827, 1989.
U.S. Pat. No. 4,935,498.
U.S. Pat. No. 5,162,509.
U.S. Pat. No. 5,252,720.
U.S. Ser. No. 08/112,872.
U.S. Ser. No. 08/227,370.
Vlassov et al., *Nucleosides & Nucleotides*, 10(103:641–643, 1991.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods, and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A method of light-induced cleavage of a polymer of deoxyribonucleic acid, the method comprising:
  contacting the polymer with a photosensitive texaphyrin; and
  exposing the photosensitive texaphyrin to light for a time sufficient to cleave the polymer.

2. The method of claim 1 wherein the exposing step is carried out in the presence of oxygen.

3. The method of claim 1 where the texaphyrin has the structure I:

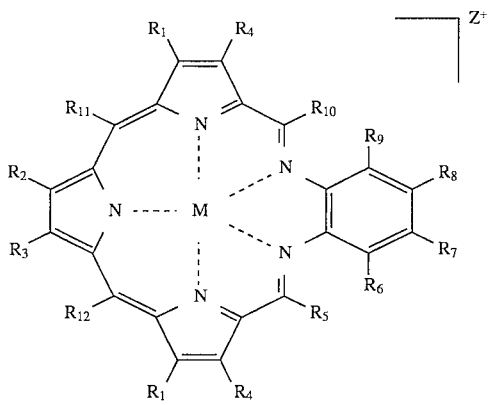

wherein,

M is H or a diamagnetic metal cation;

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamide, carboxyamidealkyl, aminoalkyl, sulfonatoalkyl, amidealkyl, aryl, a site-directing molecule, a catalytic group, or a couple to a site-directing molecule or to a catalytic group;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple to a saccharide, to a site-directing molecule or to a catalytic group; and Z is an integer less than or equal to 5.

4. The method of claim 3 wherein at least one of $R_1$–$R_{12}$ is a site-directing molecule or a couple to a site-directing molecule.

5. The method of claim 4 wherein the site-directing molecule is an oligonucleotide, a hormone, an antibody, a peptide having affinity for a biological receptor, or a sapphyrin molecule.

6. The method of claim 4 wherein the site-directing molecule is an oligonucleotide.

7. The method of claim 6 wherein the oligonucleotide is a 2'-O-alkylated ribonucleotide.

8. The method of claim 6 wherein one of $R_3$, $R_7$, and $R_8$ is an oligonucleotide or a couple to an oligonucleotide.

9. The method of claim 3 wherein $R_1$ is $CH_2CH_3$ or $(CH_2)_2CH_2OH$, $R_2$ and $R_3$ are $CH_2CH_3$, $R_4$ is $CH_3$, $R_7$ is a site-directing molecule or a couple to a site-directing molecule and $R_8$ is H, $CH_3$ or $OCH_3$.

10. The method of claim 3 wherein $R_1$ is $CH_2CH_3$ or $(CH_2)_2CH_2OH$, $R_2$ and $R_3$ are $CH_2CH_3$, $R_4$ is $CH_3$, $R_7$ is $O(CH_2CH_2O)_tCH_2CH_2OR'$ where t is 0–200 and R' is H or $CH_3$, and $R_8$ is a site-directing molecule or a couple to a site-directing molecule.

11. The method of claim 4 wherein $R_1$ is $(CH_2)_2CH_2OH$, $R_2$ and $R_3$ are $CH_2CH_3$, $R_4$ is $CH_3$, and $R_7$ and $R_8$ are $O(CH_2CH_2O)_tCH_2CH_2OR'$ where t is 0–200 and R' is H or $CH_3$.

12. The method of claim 4 wherein $R_1$–$R_{12}$ are as in Tables A–C for texaphyrins A1–A56 and B1–B22.

13. The method of claim 4 wherein M is a diamagnetic metal cation and the diamagnetic metal is Lu(III), La(III), In(III), Y(III), Zn(II) or Cd(II).

14. The method of claim 1 wherein the light has a wavelength range of about 700 to 800 nanometers.

15. The method of claim 6 wherein the oligonucleotide is a deoxyribonucleotide.

16. The method of claim 1 wherein the polymer of deoxyribonucleic acid is double-stranded DNA.

17. A method for targeted intracellular light-induced cleavage of DNA, the method comprising:

introducing into a cell a photosensitive texaphyrin coupled to an oligonucleotide having complementary binding affinity for a targeted DNA, and exposing the photosensitive texaphyrin to light for a time sufficient to effect cleavage of the DNA.

18. The method of claim 17 wherein M is a diamagnetic metal cation and the diamagnetic metal is Lu(III), La(III), In(III), Y(III), Zn(II) or Cd(II).

19. The method of claim 17 wherein the light has a wavelength range of about 700 to 800 nanometers.

20. A method for modulating the activity of a DNA, the method comprising:

contacting a DNA with a photosensitive texaphyrin coupled to an oligonucleotide having complementary binding affinity for said DNA, and exposing the photosensitive texaphyrin to light for a time sufficient to effect cleavage of the DNA.

* * * * *

UNITED STATES PATENT AND TRADEMARK OFFICE
CERTIFICATE OF CORRECTION

PATENT NO. : 5,607,924
DATED : March 4, 1997
INVENTOR(S) : Darren Magda et al.

It is certified that error appears in the above-identified patent and that said Letters Patent is hereby corrected as shown below:

At column 13, line 5, delete "RDA" and insert --DNA--.

Signed and Sealed this

Sixth Day of October, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="DNA"

( x i ) SEQUENCE DESCRIPTION: SEQ ID NO:1:

CTCGGCCATA GCGAATGTTC                    20

( 2 ) INFORMATION FOR SEQ ID NO:2:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="DNA"

( x i ) SEQUENCE DESCRIPTION: SEQ ID NO:2:

CTCGGCCATA GCGAA                         15

( 2 ) INFORMATION FOR SEQ ID NO:3:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="DNA"

( x i ) SEQUENCE DESCRIPTION: SEQ ID NO:3:

GCGCCAGAGA GGTGAGCCGG TATCGCTTAC AAGACA    36

( 2 ) INFORMATION FOR SEQ ID NO:4:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="RNA"

( x i ) SEQUENCE DESCRIPTION: SEQ ID NO:4:

CAUCUGUGAG CCGGG    15

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:5:

AAATAAAACC TCTGAAGTAG ACACTCGGCC CACAAC    36

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="RNA"

( x i ) SEQUENCE DESCRIPTION: SEQ ID NO:6:

CUCGGCCAUA GCGAA    15

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="RNA"

( x i ) SEQUENCE DESCRIPTION: SEQ ID NO:7:

UCUUCUUUCU UUUCUUU    17

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:8:

TCTTCTTTCT TTTCTTTC    18

( 2 ) INFORMATION FOR SEQ ID NO:9:

(i) SEQUENCE CHARACTERISTICS:
  (A) LENGTH: 45 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc ="DNA"

(xi) SEQUENCE DESCRIPTION: SEQ ID NO:9:

AATTCGGGCA AAAGAGTAA AAAGGAGAAG AAAGAAAAGA AACCG  45

(2) INFORMATION FOR SEQ ID NO:10:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc ="DNA"

(xi) SEQUENCE DESCRIPTION: SEQ ID NO:10:

GCCCGTTTTT CTCATTTTTC CTCTTCTTTC TTTTCTTTGG CAGCT  45